US008831887B2

(12) United States Patent
Gorfinkel et al.

(10) Patent No.: US 8,831,887 B2
(45) Date of Patent: Sep. 9, 2014

(54) ABSOLUTE PCR QUANTIFICATION

(75) Inventors: Vera Gorfinkel, Stony Brook, NY (US); Boris Gorbovitski, Stony Brook, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 1885 days.

(21) Appl. No.: 12/083,407

(22) PCT Filed: Oct. 12, 2006

(86) PCT No.: PCT/US2006/040479
§ 371 (c)(1),
(2), (4) Date: Feb. 5, 2010

(87) PCT Pub. No.: WO2007/044974
PCT Pub. Date: Apr. 19, 2007

(65) Prior Publication Data
US 2010/0137152 A1    Jun. 3, 2010

Related U.S. Application Data

(60) Provisional application No. 60/725,899, filed on Oct. 12, 2005.

(51) Int. Cl.
*G01N 33/50* (2006.01)
*B01L 7/00* (2006.01)
*G01N 21/64* (2006.01)
*C12Q 1/68* (2006.01)
*B01L 3/00* (2006.01)

(52) U.S. Cl.
CPC ..... *G01N 21/6452* (2013.01); *B01L 2300/0829* (2013.01); *B01L 7/52* (2013.01); *B01L 2300/0838* (2013.01); *B01L 2300/0816* (2013.01); *B01L 2300/069* (2013.01); *C12Q 1/6851* (2013.01); *B01L 3/50851* (2013.01)
USPC .......................................................... 702/19

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | 435/6.11 |
| 4,683,202 A | 7/1987 | Mullis | 435/91.2 |
| 4,965,188 A | 10/1990 | Mullis et al. | 435/6.12 |
| 5,210,015 A | 5/1993 | Gelfand et al. | 435/6 |
| 5,538,848 A | 7/1996 | Livak et al. | 435/6.16 |
| 5,587,128 A | 12/1996 | Wilding et al. | 422/50 |
| 5,863,736 A | 1/1999 | Haaland | 435/6 |
| 5,994,069 A | 11/1999 | Hall et al. | 435/6 |
| 6,033,880 A * | 3/2000 | Haff et al. | 435/91.1 |
| 6,126,899 A | 10/2000 | Woudenberg et al. | 422/50 |
| 6,183,960 B1 | 2/2001 | Lizardi | 435/6 |
| 6,210,884 B1 | 4/2001 | Lizardi | 435/6 |
| 6,235,502 B1 | 5/2001 | Weissman et al. | |
| 6,251,639 B1 | 6/2001 | Kurn | 435/6 |
| 6,319,469 B1 | 11/2001 | Mian et al. | 422/64 |
| 6,410,278 B1 | 6/2002 | Notomi et al. | 435/91.1 |
| 6,618,679 B2 | 9/2003 | Loehrlein et al. | 702/20 |
| 6,627,159 B1 | 9/2003 | Bedingham et al. | 422/100 |
| 6,660,517 B1 | 12/2003 | Wilding et al. | 435/287.2 |
| 6,709,869 B2 | 3/2004 | Mian et al. | 422/64 |
| 6,720,187 B2 | 4/2004 | Bedingham et al. | 436/45 |
| 7,011,944 B2 | 3/2006 | Prudent et al. | 435/6 |
| 2002/0164629 A1 * | 11/2002 | Quake et al. | 435/6 |
| 2006/0014185 A1 * | 1/2006 | Ollikka et al. | 435/6 |
| 2009/0170114 A1 * | 7/2009 | Quake et al. | 435/6 |

OTHER PUBLICATIONS de Arruda, M. et al. (2002) "Invader technology for DNA and RNA analysis: principles and applications," *Expert Rev. Mol. Diagn.* 2, 487-496.
Bustin, S. (2000) "Absolute quantification of mRNA using real-time reverse transcription polymerase chain reaction assays," *J. Mol. Endocrinol.* 25(2), 169-193.
Bustin, S. (2002) "Quantification of mRNA using real-time reverse transcription PCR (RT-PCR): trends and problems," *J. Mol. Endocrinol.* 29(1), 23-39.
Gibson, U. E. et al. (1996) "A novel method for real time quantitative RT-PCR," *Genome Res.* 6(10), 995-1001.
Heid, C. A. et al. (1996) "Real time quantitative PCR," *Genome Res.* 6(10), 986-994.
Holland, P. M. et al. (1991) "Detection of specific polymerase chain reaction product by utilizing the 5'—3' exonuclease activity of Thermus aquaticus DNA polymerase," *P.N.A.S.* 88(16), 7276-7280.
Kalinina, O. et al. (1997) "Nanoliter scale PCR with TaqMan detection," *Nucleic Acids Res.* 25(10), 1999-2004.
Klein, D. (2002) "Quantification using real-time PCR technology: applications and limitations," *Trends Mol. Med.* 8(6), 257-260.
Lagally, E. T. et al. (2001) "Fully integrated PCR-capillary electrophoresis microsystem for DNA analysis," *Lab Chip* 1(2), 102-107.
Lagally, E. T. et al. (2001) "Single-Molecule DNA Amplification and Analysis in an Integrated Microfluidic Device," *Anal. Chem.* 73(3), 565-570.
Leamon, J. H. et al. (2003) "A massively parallel PicoTiterPlate™ based platform for discrete picoliter-scale polymerase chain reactions," *Electrophoresis* 24(21), 3769-3777.
Livak, K. J. et al. (1995) "Oligonucleotides with fluorescent dyes at opposite ends provide a quenched probe system useful for detecting PCR product and nucleic acid hybridization," *Genome Res.* 4(6), 357-362.
Mitra, R. D. et al. (1999) "In situ localized amplification and contact replication of many individual DNA molecules," *Nucleic Acids Res.* 27(24), e34-e39.

(Continued)

*Primary Examiner* — Jason Sims
(74) *Attorney, Agent, or Firm* — Medlen & Carroll, LLP

(57) ABSTRACT

The present application provides methods and devices for absolute quantification of polymerase chain reaction target nucleic acids. In particular, the methods and devices of the present application provide for splitting a nucleic acid sample to be analyzed into small, isolated volumes, conducting the method of polymerase chain reaction (PCR) on said volumes, detecting PCR amplification products, analyzing said detected PCR amplification products, performing absolute quantification of the PCR target and presenting said quantification results.

14 Claims, 11 Drawing Sheets

(56) References Cited

OTHER PUBLICATIONS

Nagai, H. et al. (2001) "High-throughput PCR in silicon based microchamber array," *Biosens. Bioelectron.* 16(9-12), 1015-1019.

Pfaffl, M. W. et al. (2001) "Validities of mRNA quantification using recombinant RNA and recombinant DNA external calibration curves in real-time RT-PCR," *Biotechnol. Lett.* 23, 275-282.

Piatek, A. S. et al. (1998) "Molecular beacon sequence analysis for detecting drug resistance in *Mycobacterium tuberculosis*," *Nat. Biotechnol.* 16(4), 359-363.

Reinhold, U. et al. (2001) "Interlaboratory Evaluation of a New Reverse Transcriptase Polymerase Chain Reaction—Based Enzyme-Linked Immunosorbent Assay for the Detection of Circulating Melanoma Cells: A Multicenter Study of the Dermatologic Cooperative Oncology Group," *J. Clin. Oncol.* 19(6), 1723-1727.

Tillib, S. V. et al. (2001) "Integration of Multiple PCR Amplifications and DNA Mutation Analyses by Using Oligonucleotide Microchip," *Anal. Biochem.* 292(1), 155-160.

Tyagi, S. et al. (1998) "Multicolor molecular beacons for allele discrimination," *Nat. Biotechnol.* 16(1), 49-53.

Tyagi, S. et al. (1996) "Molecular Beacons: Probes that Fluoresce upon Hybridization," *Nat. Biotechnol.* 14(3), 303-308.

Zhu, H. et al. (1994) "High-Sensitivity Capillary Electrophoresis of Double-Stranded DNA Fragments Using Monomeric and Dimeric Fluorescent Intercalating Dyes," *Anal. Chem.* 66(13), 1941-1948.

\* cited by examiner

FIGURE 2
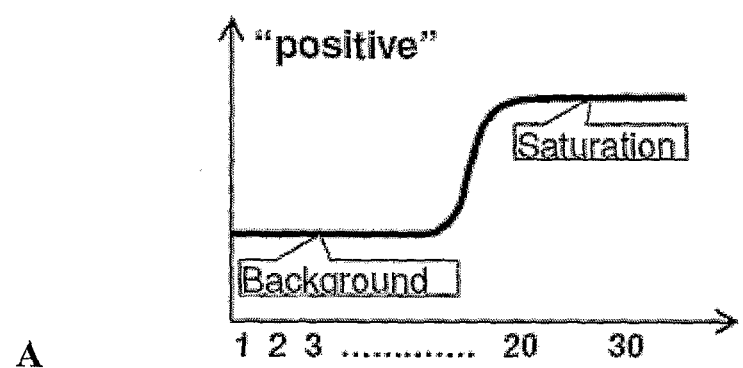
A
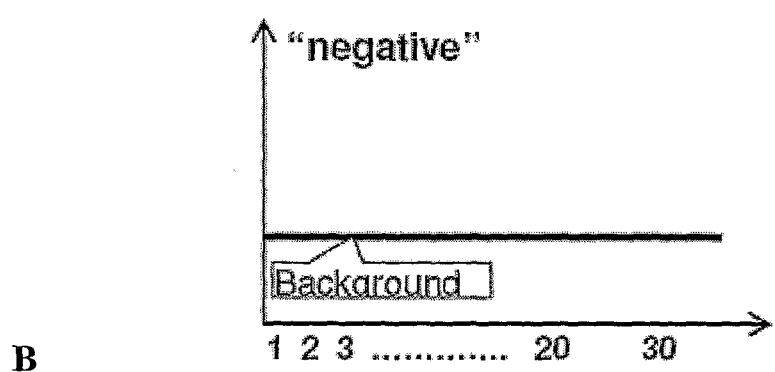
B

FIGURE 3
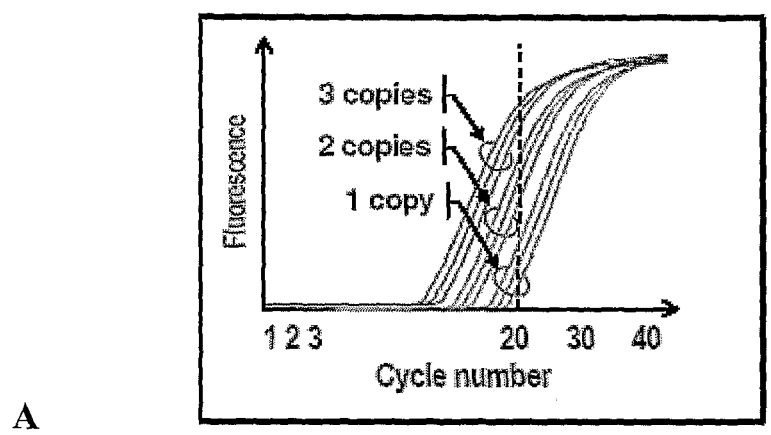
A
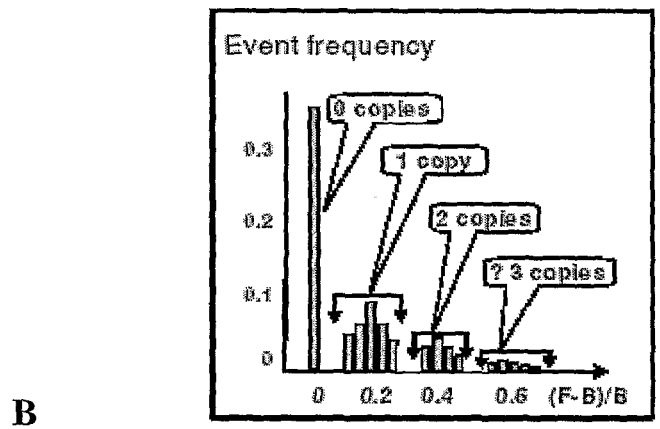
B
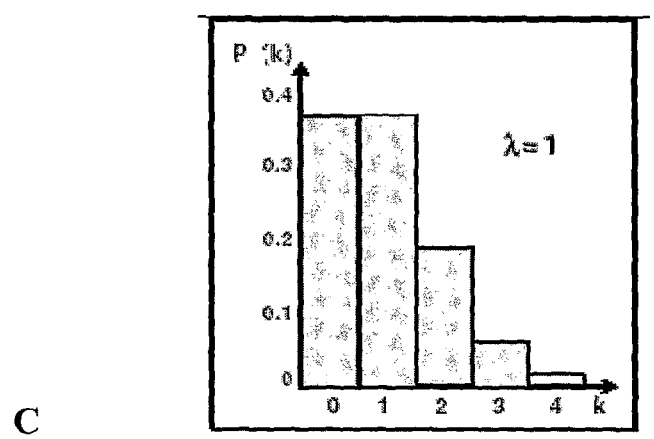
C

FIGURE 6
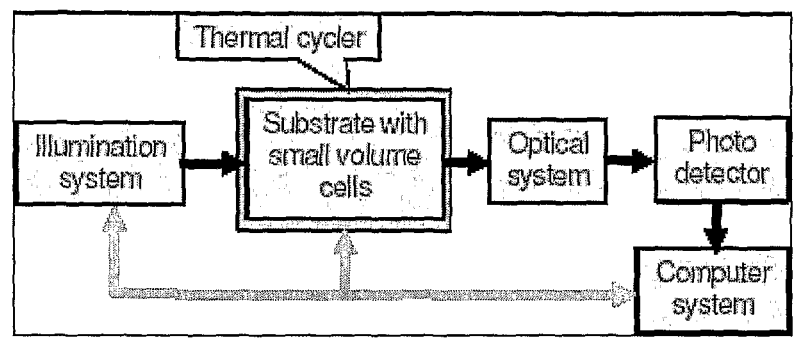
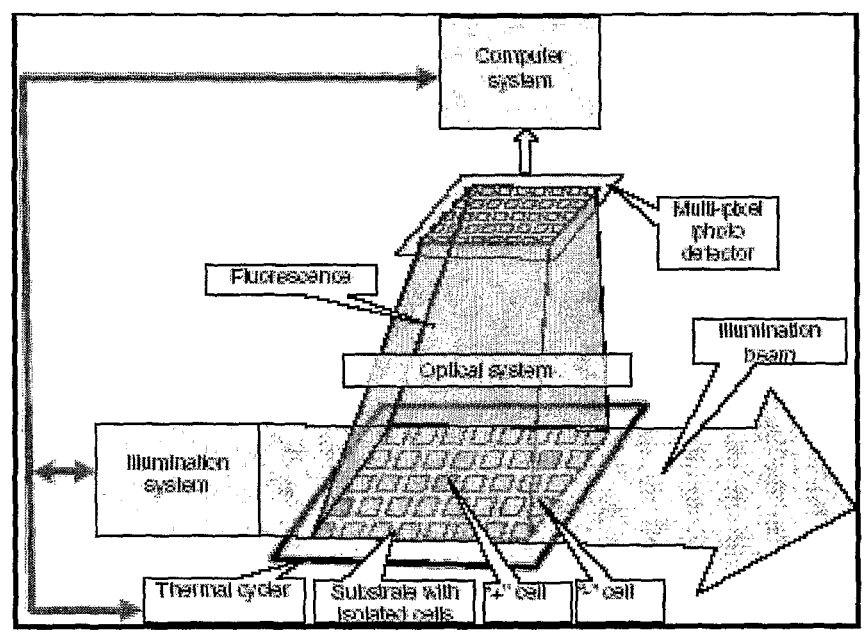

FIGURE 9

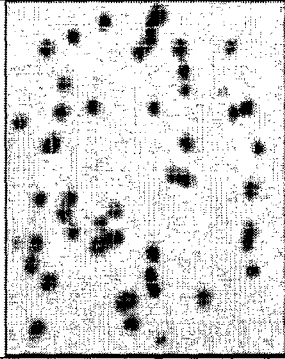

| Number of template DNA molecules =60 | Number of template DNA molecules =180 | Number of template DNA molecules =360 |
|---|---|---|
| Calculation | Calculation | Calculation |
| Total grid cells  N=342<br>Empty cells  m=290<br>$\lambda_{EST}=-\ln(290/342)=0.165$<br>$m_1=342\times0.165\approx56$ | Total grid cells  N=360<br>Empty cells  m=220<br>$\lambda_{EST}=-\ln(220/360)=0.492$<br>$m_1=360\times0.492\approx177$ | Total grid cells  N=360<br>Empty cells  m=132<br>$\lambda_{EST}=-\ln(132/360)=1.03$<br>$m_1=360\times1.03\approx361$ |

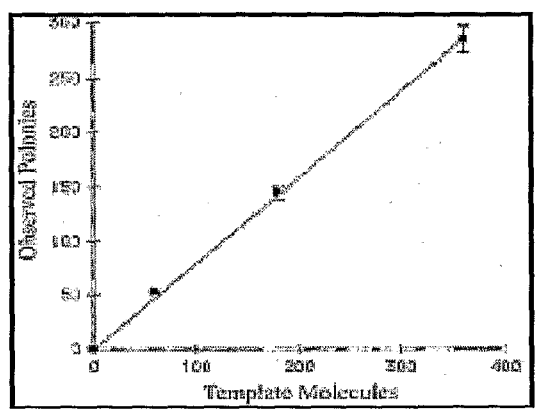

ABSOLUTE PCR QUANTIFICATION

CROSS-REFERENCE TO RELATED APPLICATIONS

The present application, as a national state application, claims the benefit of PCT Application No. PCT/US06/40479, filed Oct. 12, 2006 and to U.S. Provisional Application No. 60/725,899, filed Oct. 12, 2005, which are both incorporated herein by reference.

FIELD OF THE INVENTION

The present application provides methods and devices for absolute quantification of polymerase chain reaction target nucleic acids. In particular, the methods and devices of the present application provide for splitting a nucleic acid sample to be analyzed into small, isolated volumes, conducting the method of polymerase chain reaction (PCR) on said volumes, detecting PCR amplification products, analyzing said detected PCR amplification products, performing absolute quantification of the PCR target and presenting said quantification results.

BACKGROUND OF THE INVENTION

Real-time PCR has become the method of choice in various gene-related applications because it is conceptually straightforward, flexible and sensitive while generating quantitative data (Heid et al., 1996, Genome Res. 6:986). Its applicability as an important diagnostic tool has been demonstrated in many clinical applications (e.g., Bustin, 2002, J. Mol. Endo. 29:23). However, its inherent wide variability of results (Reinhold et al., 2001, J. Clin. Onc. 19:1723) still makes it unreliable in clinical diagnostics. The major drawback is that all known real-time PCR methods (and instruments) have not yet achieved the levels of sensitivity, fidelity, accuracy, reproducibility and resolution necessary for true absolute quantification of low abundance targets. Moreover, new reagents, chemistries and instruments continuously introduced into the real-time PCR field make it increasingly difficult to compare results obtained in different laboratories and at different times (Bustin, 2002).

Quantification of an amplified target in "real-time" PCR is based on measuring the reaction product by sampling its fluorescence in the reaction mix during the course of the amplification reaction, generally at each cycle (Heid et al., 1996). The fluorescence gives a measure of the reaction's kinetics, which allows building a kinetic curve for the reaction and assessing a linearity range for the reaction (e.g., in logarithmic scale). In order to estimate the amount of the target nucleic acid prior to amplification (e.g., the number of original copies of the target, prior to amplification), one only needs a calibration curve, which is built from a series of kinetic curves recorded for the target nucleic acid at known target dilutions. The calibration curve is then used to estimate the concentration of target in unknown samples, on the assumption that the reaction kinetics (the efficiencies of amplifying the target materials) for each calibration dilution are the same, and that they are equal to those in the experimental sample. This in turn requires the calibration curve to be linear on a logarithmic scale.

Quantification of the real-time PCR is centered on the assumption that the fluorescence recorded at each cycle represents the amount of the amplified target DNA. Fluorescence of a sample is normalized to that of an internal reference fluorophore to correct for fluctuations in volume and/or concentration and recorded as a point on a kinetic curve. The point at which the fluorescent signal is first recorded as statistically significant above the background is defined as threshold cycle (Ct). It is assumed that Ct occurs during the exponential phase of the PCR, so that quantification is not affected by biases of the plateau phase. The Ct value is reported for each sample and then made into a quantitative result, e.g., the initial target concentration or number of target copies is estimated by comparison to an external calibration (or "standard") curve.

An inherent problem when using a calibration or standard curve is that the reaction saturates very quickly, and background fluorescence in the absence of amplification is typically very high. Early detection is precluded by high background fluorescence that occurring the absence of amplification. This is because the level of noise associated with the background is higher than the useful signal generated by the PCR product on early cycles, which makes the PCR product effectively undetectable at the beginning of the reaction. Also, for the product quantification using a calibration or standard curve, it is assumed that during the early amplification cycles the reaction efficiency (i.e., fold increase per cycle) is the same as in later cycles.

There are currently two major approaches to PCR quantification: relative and absolute. Relative quantification is used to determine the changes in nucleic acid levels (e.g., differences between samples of different kinds, or in cells that have been differently treated). For a relative calibration curve, a series of dilutions of a calibrator sample are used. The calibrator can be any nucleic acid with known concentration and amplicon length. During PCR amplification, Ct numbers for the calibrator dilutions are detected and plotted against arbitrary units. The target Ct numbers are applied directly to the calibration curve, and the result is expressed as fold increase or decrease relative to the reference measurement.

In contrast, absolute quantification seeks to determine the number of target copies initially present in a sample. It requires the building of an absolute calibration curve for each individual amplicon as a measure of the efficiencies of amplification during all amplification steps, including the reverse transcription step (e.g., when performing reverse transcription PCR, RT-PCR) and during PCR amplification. Since the standard template must be pure (i.e., a standard free from non-target RNA/DNA contamination), it is usually prepared from recombinant DNA or RNA. Serial dilutions of the DNA/RNA standard are prepared, and each dilution is re-assayed in the same PCR run along with experimental samples and positive and negative controls. Ct values for each standard dilution are recorded and a standard curve is generated by plotting the Ct values against the logarithm of the initial copy numbers, which are inversely proportional to each other. The initial target copy number (TCN) of the experimental sample is calculated using a linear regression equation of that calibration curve and Ct values for the experimental sample. Because of the sample-to-sample variations in the amount of starting material, especially in clinical samples, the results are normalized by tissue mass, cell number, or nucleic acid amount (e.g., total DNA or RNA, ribosomal RNA, or cDNA/mRNA of for example, housekeeping genes) (Bustin, 2002; Bustin, 2002, J. Mol. Endo. 25:169).

Although the objective is to identify a precise initial TCN, absolute quantification of the real-time PCR method has a principle flaw in that it is based on an external calibration. The external calibration requires ideal validation of identical reaction kinetics (i.e. amplification efficiencies) for the calibrator template and the target template (Pfaffl and Hageleit, 2001, Biotech. Lett. 23:275; Klein, 2002, Trends Mol. Med. 8:257).

Such validation is extremely difficult, even for ideal samples, let alone experimental and clinical samples from different laboratories and testing sites, different tissues, animals and patients. In addition, clinical samples can vary widely in purity, making it very difficult to provide truly identical reaction conditions for both the purified control and the clinical sample.

The accuracy of the absolute quantification method depends heavily on a few critical assumptions. The first assumption is that targets and calibrators are amplified with the same efficiency. Another assumption is that the efficiencies for calibrator and target detected at Ct are identical to those in the earlier cycles. However, clinical samples often contain contaminants and/or inhibitors that reduce the efficiency of the amplification reaction compared to the pristine samples used as calibrator templates. In addition, inhibitors appear to have a stronger effect in the earlier cycles (they may degrade, e.g., by exposure to the extreme temperature of PCR, by the later cycles), which then results in underestimation of the copy number for a reaction. The exponential nature of the PCR, combined with a small number of the target molecules leads to a situation where small variations in efficiencies during the early cycles causes great variations of the final yield of the amplified product (Bustin, 2002). As a result, PCR-based quantification is often characterized by significant variations and non-reproducibility. Therefore, a large variety of enzymes, primers, and test samples, and the absence of acceptable validation and normalization procedures leads to poor reproducibility of data in different laboratories and raises serious doubts about how quantitative, reproducible or statistically informative real-time PCR is (e.g., Bustin 2002). Therefore, the usefulness and reliability of using quantitative real-time PCR as a routine clinical diagnostic is questionable (Bustin 2000, 2002; Klein 2002; Pfaffl and Hageleit, 2001).

PCR is, to date, the best method for detecting low abundance nucleic acid molecules. However, the statistics of particle distribution predicts that quantification of small numbers of molecules makes Ct data less reproducible due to stochastic effects (Rasmussen, R (2001) Quantification on the Light-Cycler. In: Meuer, S, Wittwer, C, Nakagawara, K, eds. Rapid Cycle Real-time PCR, Methods and Applications. Springer Press, Heidelberg; p. 21-34) which, in combination with all the other drawbacks as previously listed, makes quantification of the low abundance target even less reliable.

There exists a PCR-based method to assess directly the small numbers of DNA/RNA molecules. The approach is based on competitive end-point PCR of multiple sub-microliter samples containing two terminally diluted targets labeled with different fluorescent markers excitable at different wavelengths (e.g., a control target of known TCN and an unknown target of unknown TCN). Following PCR amplification, the samples undergo relative quantification of the two targets (e.g., either by capillary electrophoresis, Lagally et al., 2001, Anal. Chem. 73:565; Lagally et al., 2001, Lab on a Chip, 1:102, or fluorescence detection by confocal microscope, Kalinina et al., 1997, Nucl. Acids Res. 25:1999). The distribution function of the amplified product is analyzed using Poisson statistics best-fit method. Although the described approach enables a statistically significant absolute quantification of the TCN in the original sample and does not require any external calibration, it relies on the relative quantification of the control and the target components after the end-point PCR. This by itself lowers the quantification accuracy and makes the method both time and labor consuming. This approach has been utilized to demonstrate single copy. PCR amplification (Lagally et al., 2001; Kalinina et al., 1997). It has not become a routine quantitative method because, in order to collect statistics sufficient for accurate target quantification, it requires rather complicated sample handling and the detection of hundreds of separate PCR amplification reactions.

Efforts in improving quantitative PCR also include the desire to minimize the time-to-result and the cost per result. Approaches generally include decreasing the amplification reaction volume and at the same time increasing the number of reactions that are performed simultaneously (e.g., by use of high throughput systems). The microchamber army for PCR amplification described by Nagai et al. (2001, Biosens. Bioelec. 16:1015) demonstrated that high-throughput, rapid, synchronous amplification of multiple amplification targets was possible. The PicoTiterPlate™ as described by Leamon et al., 2003, Electophoresis 24:3769, further demonstrated that amplification using low reaction volumes (as low as 39.5 µl) and low starting template copy number (calculated as 5 copies of template per reaction) in a high throughput format (up to 300,000 discrete reactions on one plate) was possible. Leamon goes one step further and describes his method as being a method for quantitative PCR. However, the quantitative PCR of Leamon is a relative and not absolute quantification, in that a standard curve was generated and fluorescence readings were applied to the curve to define amplicon fold increase in an end-point PCR assay.

The BioMark™ system developed by Fluidigm Corporation (San Francisco, Calif.) advertises a nanofluidic chip reported to absolutely quantify target nucleic acids (Application Marketing Note MRKT00047.VD). The literature describes constant amplification monitoring via fluorescence detection, such that the system is a real-time PCR system. However, when calculations are performed on the data as described, mathematical analysis does not bear out the conclusions, i.e., absolute quantification of the sample template was not, in fact, realized. The results as listed do not satisfy a Poisson distribution curve (i.e., bell-shaped curve). For example, when taking the white counts found in FIG. 2, 5 pg DNA slide (count=310) and applying the Poisson probability equation, the $\lambda$ parameter (i.e., a shape parameter that indicates the average number of events in a given time period) is calculated to be $\lambda=0.25$, indicating that the white compartment counts found in FIG. 2 should be around 273, which differs from the reported results by two standard deviations-outside the range of random probability. When calculating the $\lambda$ parameter of the 1 pg DNA slide (count-62), $\lambda=0.50$. Therefore, the disparity in the average number of events in a given time period and data reported that is actually outside the range of random probability demonstrates that, under the experimental conditions reported, absolute quantification of target nucleic acids has not occurred.

As such, the lack of automated, reliable, absolute quantification in nucleic acid amplification methods is a huge obstacle for introducing these methods in clinical diagnostics where the problems are multiplied by, for example, variations in samples from different patients, sample collection conditions, and technical loading errors. This variation makes it practically impossible to relate the results from, for example, different laboratories, methods, patients and tissues in terms of target copy number. Consequently, it is impossible to establish databases originating from PCR results obtained in various studies and proves to be a critical impediment for utilizing real time PCR as a clinical tool.

Therefore, what are needed are new methods and devices that provide approaches for high-throughput, highly accurate nucleic acid quantification such that direct, absolute quantification of target amplicons is realized. Such methods and devices will not only aide in bringing continuity and consistency to clinical diagnostics, but also serve as improved research tools for the scientific community as they perform the needed research to decipher the genes and related sequences that impact daily lives.

SUMMARY OF THE INVENTION

The present application provides methods and devices for absolute quantification of target nucleic acids. In particular, the methods and devices of the present application provide for splitting a nucleic acid sample to be analyzed into small, isolated volumes, conducting the method of nucleic acid detection on said volumes, analyzing the detection results, performing absolute quantification of initial amount of target nucleic acid in the sample, and presenting said quantification results.

In one embodiment, the present invention provides for a method of counting target nucleic acid molecules comprising providing a sample containing a plurality of target nucleic acid molecules, applying said sample to a multiple vessel array wherein the multiple vessel array comprises a plurality of reaction vessels, wherein each of said reaction vessels receives an essentially equal sub-volume of the aforementioned sample, wherein the combined volumes of said sub-volumes defines a tested volume and wherein the number of said plurality of reaction vessels is comparable with the number of target nucleic acid molecules in said tested volume, treating said multi vessel array to conditions to produce a detectable signal in the presence of said target nucleic acid, and determining how many of said reaction vessels contain reactions producing said detectable signal. In some embodiments, the ratio of target molecules to reaction vessels is 10:1, 3:1, 2:1, 1:1, 0.5:1, 0.1:1 or 0.01:1. In some embodiments, said multiple vessel array comprise at least 100 reaction vessels, at least 500 reaction vessels, or at least 1000 reaction vessels. In some preferred embodiments, said multiple vessel array is a multiple capillary array, wherein said reaction vessels are capillary reaction vessels. In some preferred embodiments, the individual reaction vessels have volumes of less than 1 µl. In particularly preferred embodiments, the individual reaction vessels have volumes of less than 1 nanoliter.

In some embodiments, said determining comprises determining how many of said reaction vessels contain reactions that do not produce said detectable signal.

In some embodiments, said conditions comprise exposure of said target nucleic acid to reagents for producing a detectable signal in the presence of said target nucleic acid. In some embodiments, the sample further comprises the nucleic acid detection reagents. In some embodiments, said multiple vessel array further comprises said reagents. In some preferred embodiments, the multiple vessel array comprises the reagents and the reagents are dried prior to exposure to a liquid sample. In some preferred embodiments, the reagents are reagents for performing a nucleic acid amplification reaction. In particularly preferred embodiments, the nucleic acid amplification reaction is a polymerase chain reaction. In some embodiments, said determining is conducted after the completion of a polymerase chain reaction.

In some embodiments, the detectable signal comprises fluorescence. In some embodiments, the reagents comprise an oligonucleotide probe comprising a fluorescent moiety. In some preferred embodiments, the oligonucleotide probe further comprises a quencher moiety. In some embodiments, the reagents comprise a nucleic acid intercalating dye.

In some embodiments, the polymerase chain reaction is conducted for a predetermined number of cycles, wherein said determining is conducted after completion of the predetermined number of cycles.

In some embodiments, the number of target molecules is calculated using the equation:

$$M_0 = N_{sub-volumes} \times [-\ln(P)]$$

wherein $M_0$ is the number of target molecules in said tested volume,
wherein N is the number of sub-volumes, and
wherein P is the percent of sub-volumes lacking the detectable signal.

In some embodiments, a standard deviation for the number of target molecules in a tested volume is calculated using the equation:

$$\sigma_N = \sqrt{N_{sub-volumes} P(1-P)}$$

wherein $\sigma_N$ is the standard deviation.

In some embodiments, the sample is a test sample, and the method further comprises providing a negative control sample lacking said target nucleic acid, wherein said negative control sample is tested in parallel and is treated identically to said test sample, wherein a Poisson parameter for said test sample is estimated using the equation:

$$\lambda_{EST} = \ln[P_{CONTROL}(0)/P_{SAMPLE}(0)]$$

wherein
$\lambda_{EST}$ is the estimated Poisson parameter for said test sample
$P_{CONTROL}(0)$ is the percent of reaction vessels lacking signal in the control negative assay
$P_{SAMPLE}(0)$ is the percent of reaction vessels lacking signal in said test DNA sample.

In some embodiments, the method further comprises communication of the number of capillary reaction vessels in which it is determined that the reagents produced no detectable signal to a computer, wherein the calculations described above are performed by the computer.

In one embodiment, the present invention provides a device for testing a nucleic acid sample wherein said device comprises a multiple capillary array comprising a first plurality of capillary reaction vessels, wherein each of said first plurality of capillary reaction vessels is configured to receive an essentially equal sub-volume of an applied liquid sample. In some embodiments, said capillary reaction vessels are essentially parallel to each other. In some embodiments, said device further comprises a filling groove and at least one vent groove, wherein said filling groove is fluidically connected to each of said capillary reaction vessels in said first plurality of capillary reaction vessels. In some embodiments, said multiple capillary array comprises one or more additional pluralities of capillary reaction vessels wherein each of the additional pluralities of capillary reaction vessels is fluidically connected to a filling groove to which no other pluralities of capillary reaction vessels are connected. In some embodiments, said pluralities of capillary reaction vessels are separated from one another by zone separators.

In some embodiments, said device further comprises a component for temperature cycling said capillary reaction vessels. In some embodiments, said device further comprises a fluorescence detector. In some embodiments, said device further comprises a computer operably linked to said fluorescence detector. In further embodiments, the fluorescence detector is configured to detect fluorescence during temperature cycling, while in other embodiments, the fluorescence detector is configured to detect fluorescence only when the component is not temperature cycling.

In one embodiment, the present invention provides a method of sampling a target nucleic acid, comprising providing a sample tray comprising a plurality of isolated reaction zones, wherein each isolated reaction zone contains a nucleic acid binding agent having a specific nucleic acid binding rate, and wherein the binding rates of the binding agents in different isolated reaction zones are variable binding rates, exposing the sample tray to a sample comprising target nucleic acid under conditions wherein each isolated reaction zone is exposed to said sample for essentially the same amount of time, removing unbound target nucleic acid from said sample tray, and detecting the target nucleic acid in said isolated reaction zones. In some embodiments, said variable binding rates are serial binding rates. In further embodiments, the serial binding rates differ between isolated reaction zones by factors of 2, by factors of 5, by factors of 10, by factors of 100, or by factors of 1000.

In some embodiments, said nucleic acid binding agent comprises a gel matrix. In some embodiments, the specific nucleic acid binding rate of said gel matrix is determined by the rate at which nucleic acid diffuses through said gel matrix. In some embodiments, the gels matrices in said different isolated reaction zones have different gel porosities. In some embodiments, the gels matrices in said different isolated reaction zones have different gel volumes.

In one embodiment, the present invention provides a method of sampling a target nucleic acid comprising providing a sample tray comprising a plurality of isolated reaction zones wherein each isolated reaction zone contains a nucleic acid binding agent having a specific nucleic acid binding capacity and wherein the binding capacities of the binding agents in different isolated reaction zones are variable binding capacities, exposing the sample tray to a sample comprising target nucleic acid under conditions wherein said binding agent binds to said target nucleic acid, removing unbound target nucleic acid from said sample tray, and detecting the target nucleic acid in said isolated reaction zones. In some embodiments, said variable binding capacities are serial binding capacities. In some embodiments, the serial binding capacities differ between isolated reaction zones by factors of 2, by factors of 5, by factors of 10, by factors of 100, or by factors of 1000.

In one embodiment, the present invention provides a method of sampling a target nucleic acid comprising providing a sample tray comprising a plurality of isolated reaction zones wherein each isolated reaction zone defines a specific reaction sub-volume and wherein the reaction sub-volumes of said different isolated reaction zones are variable reaction sub-volumes, exposing the sample tray to a sample comprising one or more target nucleic acid molecules under conditions wherein sample fills said plurality of isolated reaction zones, and detecting the target nucleic acid in said isolated reaction zones. In some embodiments, said variable reaction sub-volumes are serial reaction sub-volumes. In some embodiments, the serial reaction sub-volumes differ between isolated reaction zones by factors of 2, by factors of 5, by factors of 10, by factors of 100, or by factors of 1000.

In some embodiments, said sample comprises reagents for a nucleic acid detection reaction. In further embodiments, said detecting comprises performing a nucleic acid detection reaction. In some embodiments, said nucleic acid detection reaction comprises a nucleic acid amplification reaction. In some embodiments, said nucleic acid amplification reaction is a polymerase chain reaction. In some embodiments, said detecting is conducted after the completion of said polymerase chain reaction. In further embodiments, said detecting for said sampling a target nucleic acid comprises detection of fluorescence. In some embodiments, said reagents comprise an oligonucleotide probe comprising a fluorescent moiety. In some embodiments, said oligonucleotide probe further comprises a quencher moiety. In some embodiments, said reagents comprise a nucleic acid intercalating dye. In some embodiments, said polymerase chain reaction is conducted for a predetermined number of cycles and said detecting is conducted after completion of said predetermined number of cycles.

DESCRIPTION OF THE DRAWINGS

FIGS. 2A and B show real-time PCR curves (fluorescence on the y-axis vs. PCR cycle number on the x-axis) recorded from positive or "YES" (A) and negative, or "NO" (B) cells.

FIGS. 3A, B and C demonstrate typical PCR curves; (A) of different starting template copy number (fluorescence on the y-axis vs. PCR cycles number on the x-axis), (B) a histogram of fluorescence signal with fluorescence minus background B (x-axis) detected in individual sub-volumes (y-axis), and (C) a Poisson distribution of initial copy numbers (ONTMs) in individual sub-volumes for average $\lambda=1$.

FIG. 6 illustrates an embodiment of the present invention. The template sample is diluted in PCR mix containing fluorescent labels and distributed on the substrate between small-volume cells. It is done so that the average number of target copies per one cell $\lambda$ is low. The substrate undergoes thermal cycling. Cells on the substrate are illuminated by an illumination system (e.g., laser) and emitted fluorescence image of the device is projected through the optical system onto multi-pixel photodetector (e.g., CCD, CMOS detector, PMT, or APD array) and recorded by the computer system. Statistical analysis of "+" and "−" events yields $\lambda$, from which ONTM is calculated and reported.

FIG. 9 demonstrates that the calculation of the number of polonies based on the count of empty cells as described herein yields a more accurate polony count than the manually counted (observed count) polonies as performed in Metra and Church (1999, Nucl. Acids Res. 27:e34). For example, comparing the left panel plot and $m_1$ values obtained through calculated Poisson statistics to observed polonies for the number of template molecules (graph) shows a discrepancy between the polonies counted and those calculated. The discrepancy between the number of template DNA molecules and the observed (counted) number of polonies increases with an increase in the concentration of template DNA, as shown when comparing the 180 and 360 template molecule panel calculations with those observed as plotted in the graph.

DEFINITIONS

Figure 1:
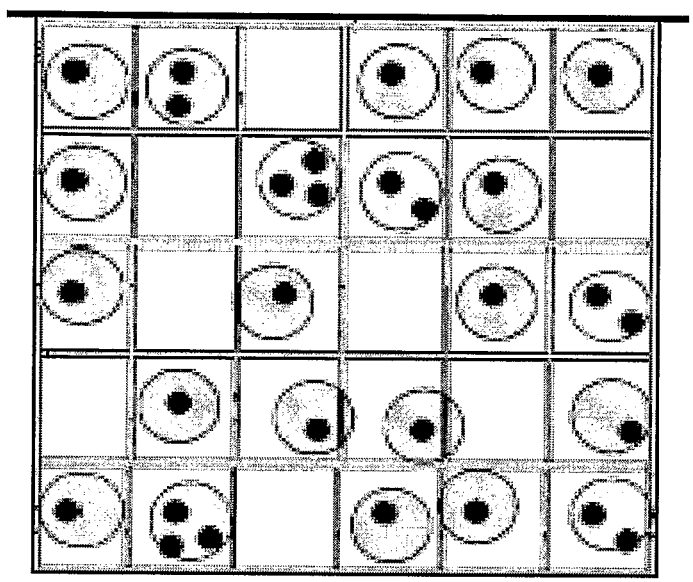
FIG. 1 shows a characterization of PCR products (gray circles) obtained in small isolated sub-volumes from different number of target copies (black circles).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxy-amino-methyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "Poisson statistics", or "Poisson distribution" describes, through mathematics, a discrete probability distribution. It expresses the probability of a number of events occurring in a fixed period of time if these events occur with a known average rate and are independent of the time since the last event. For example, the present invention presents devices and methods for performing and calculating the original number of template molecules in a PCR reaction that satisfy Poisson statistics, thereby yielding absolute quantification of the original number of template molecules present at the beginning of an amplification reaction.

The term "target," when used in reference to a nucleic acid detection or analysis method, refers to a nucleic acid having a particular sequence of nucleotides to detected or analyzed, e.g., in a sample suspected of containing the target nucleic acid. When used in reference to the polymerase chain reaction, "target" generally refers to the region of nucleic acid bounded by the primers used for polymerase chain reaction. Thus, the "target" is sought to be sorted out from other nucleic acid sequences that may be present in a sample. A "segment" is defined as a region of nucleic acid within the target sequence. The term "sample template" refers to nucleic acid originating from a sample that is analyzed for the presence of a target.

As used herein, the term "genotype" refers to the actual genetic make-up of an organism (e.g., in terms of the particular alleles carried at a genetic locus). Expression of the genotype gives rise to an organism's physical appearance and characteristics—the "phenotype."

As used herein, the term "locus" refers to the position of a gene or any other characterized sequence on a chromosome.

As used herein the term "disease" or "disease state" refers to a deviation from the condition regarded as normal or average for members of a species, and which is detrimental to an affected individual under conditions that are not inimical to the majority of individuals of that species (e.g., diarrhea, nausea, fever, pain, and inflammation etc).

As used herein, the term "treatment" in reference to a medical course of action refer to steps or actions taken with respect to an affected individual as a consequence of a suspected, anticipated, or existing disease state, or wherein there is a risk or suspected risk of a disease state. Treatment may be provided in anticipation of or in response to a disease state or suspicion of a disease state, and may include, but is not limited to preventative, ameliorative, palliative or curative steps. The term "therapy" refers to a particular course of treatment.

The term "gene" refers to a nucleic acid (e.g., DNA) sequence that comprises coding sequences necessary for the production of a polypeptide, RNA (e.g., rRNA, tRNA, etc.), or precursor. The polypeptide, RNA, or precursor can be encoded by a full length coding sequence or by any portion of the coding sequence so long as the desired activity or functional properties (e.g., ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments included when a gene is transcribed into heterogeneous nuclear RNA (hnRNA); introns may contain regulatory elements such as enhancers. Introns are removed or "spliced out" from the nuclear or primary transcript; introns therefore are generally absent in the messenger RNA (mRNA) transcript. The mRNA functions during translation to specify the sequence or order of amino acids in a nascent polypeptide. Variations (e.g., mutations, SNPS, insertions, deletions) in transcribed portions of genes are reflected in, and can generally be detected in corresponding portions of the produced RNAs (e.g., hnRNAs, mRNAs, rRNAs, tRNAs).

Where the phrase "amino acid sequence" is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," and "variant" refer to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. In this case, the DNA sequence thus codes for the amino acid sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" ("PCR"). Because the desired amplified segments of the target sequence become the predominant sequences (in terms of concentration) in the mixture, they are said to be "PCR amplified" and are "PCR products" or "amplicons."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment, fluorescently labeled primers, incorporation of fluorophore into PCR products during the amplification process or after cycling is completed). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "real-time PCR" is used to describe the detection of amplification products throughout the amplification process. For example, it may be desirable to measure the accumulation of PCR products after each cycle, or after selected numbers of cycles during the ongoing reaction (e.g., after 4 cycles, after 6 cycles, after 8 cycles, etc.). Using real time PCR, the progress and efficiency of the amplification reaction can be monitored while it is occurring.

As used herein, the term "end point PCR" is used to describe the detection of the amplification products at the end of a PCR assay. For example, if a PCR assay was designed to contain 30 PCR cycles, an end point PCR assay would detect the accumulation of amplification products after the 30 cycles has been completed. Using end point PCR, accumulation of amplicons is determined only when PCR is completed.

As used herein, the term "amplification reagents" refers to those reagents (deoxyribonucleotide triphosphates, buffer, etc.), needed for amplification. Typically, amplification reagents along with other reaction components are placed and contained in a reaction vessel, for example a device of the present invention.

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, the term "gel substrate" refers to a substrate that is capable of allowing the diffusion of nucleic acid molecules, while allowing for PCR to occur within the substrate. For example, a gel substrate of the present invention could be gelatin, agarose, Matrigel®, collagen, and other types of polymers capable of allowing for nucleic acid diffusion and PCR amplification.

As used herein, the term "probe" or "hybridization probe" refers to an oligonucleotide (i.e., a sequence of nucleotides), whether occurring naturally as in a purified restriction digest or produced synthetically, recombinantly or by PCR amplification, that is capable of hybridizing, at least in part, to another oligonucleotide of interest. A probe may be single-stranded or double-stranded. Probes are useful in the detection, identification and isolation of particular sequences. In some preferred embodiments, probes used in the present invention will be labeled with a "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "sample" as used herein is used in its broadest sense. For example, a sample suspected of containing a human gene or chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like.

The term "signal" as used herein refers to any detectable effect, such as would be caused or provided by a label or an assay reaction.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the term "detector" refers to a system or component of a system, e.g., an instrument (e.g. a camera, fluorimeter, charge-coupled device, scintillation counter, etc.) or a reactive medium (X-ray or camera film, pH indicator, etc.), that can convey to a user or to another component of a system (e.g., a computer or controller) the presence of a signal or effect. A detector can be a photometric or spectrophotometric system, which can detect ultraviolet, visible or infrared light, including fluorescence or chemiluminescence; a radiation detection system; a spectroscopic system such as nuclear magnetic resonance spectroscopy, mass spectrometry or surface enhanced Raman spectrometry; a system such as gel or capillary electrophoresis or gel exclusion chromatography; or other detection system known in the art, or combinations thereof.

.The term "detection" as used herein refers to quantitatively or qualitatively identifying an analyte (e.g., DNA, RNA or a protein) within a sample. The term "detection assay" as used herein refers to a kit, test, or procedure performed for the purpose of detecting an analyte nucleic acid within a sample. Detection assays produce a detectable signal or effect when performed in the presence of the target analyte, and include but are not limited to assays incorporating the processes of hybridization, nucleic acid cleavage (e.g., exo- or endonuclease), nucleic acid amplification, nucleotide sequencing, primer extension, or nucleic acid ligation.

As used herein, the term "detection assay component" refers to a component of a system capable of performing a detection assay. Detection assay components include, but are not limited to, hybridization probes, buffers, and the like.

As used herein, the term "a detection assay configured for target detection" refers to a collection of assay components that are capable of producing a detectable signal when carried out using the target nucleic acid. For example, a detection assay that has empirically been demonstrated to detect a particular single nucleotide polymorphism is considered a detection assay configured for target detection.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

As used herein, the term "information" refers to any collection of facts or data. In reference to information stored or processed using a computer system(s), including but not limited to internets, the term refers to any data stored in any format (e.g., analog, digital, optical, etc.). As used herein, the term "information related to a subject" refers to facts or data pertaining to a subject (e.g., a human, plant, or animal). The term "genomic information" refers to information pertaining to a genome including, but not limited to, nucleic acid sequences, genes, allele frequencies, RNA expression levels, protein expression, phenotypes correlating to genotypes, etc. "Allele frequency information" refers to facts or data pertaining allele frequencies, including, but not limited to, allele identities, statistical correlations between the presence of an allele and a characteristic of a subject (e.g., a human subject), the presence or absence of an allele in a individual or population, the percentage likelihood of an allele being present in an individual having one or more particular characteristics, etc.

As used herein, the term "reaction vessel" refers to a system in which a reaction may be conducted, including but not limited to test tubes, wells, microwells (e.g., wells in microlitre assay plates such as, 96-well, 384-well and 1536-well assay plates), capillary tubes, ends of fibers such as optical fibers, microfluidic devices such as fluidic chips, cartridges and cards (including but not limited to those described, e.g., in U.S. Pat. No. 6,126,899, to Woudenberg, et al., U.S. Pat. Nos. 6,627,159, 6,720,187, and 6,734,401 to Bedingham, et al., U.S. Pat. Nos. 6,319,469 and 6,709,869 to Mian, et al., U.S. Pat. Nos. 5,587,128 and 6,660,517 to Wilding, et al.), or a test site on any surface (including but not limited to a glass, plastic or silicon surface, a bead, a microchip, or an non-solid surface, such as a gel or a dendrimer).

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refers to a device that is able to read a program from a computer memory (e.g., ROM or other computer memory) and perform a set of steps according to the program.

As used herein, the term "fluidic connection" refers to a continuous fluid path between components, e.g., between a filling groove and a reaction vessel such as a capillary reaction vessel.

As used herein, the term "parallel" in reference to processes, reactions, etc., refers to processes or actions functioning in an essentially simultaneous, side-by-side, manner (e.g., parallel PCR reactions).

As used herein, the term "parallel" as used in reference to a plurality of physical components or objects refers to the geometrical relationship between the objects. For example, a capillary tube or vessel having an essentially linear form is said to be parallel to a second capillary of the same form when the pair of capillaries are oriented in the same direction, such that they are geometrically parallel to each other.

As used herein, the term "multiple vessel array" refers to a collection of reaction vessels configured for simultaneous processing of multiple sub-volumes of a sample, e.g., for conducting multiple detection reactions on sub-volumes of the same sample, in parallel (at the same time, under the same conditions). A multiple vessel array is further configured to distribute said sample into each of said reaction vessels, e.g., through fluidic connection to a sample loading system such as a filling groove, such that a single application of sample to the array can fill each vessel in said multiple vessel array. The multiple vessel array is not limited to any particular number or configuration of vessels, e.g., it may comprise, 2, 10, 100, 1000, or any other number greater than 2. A single device may comprise more than one multiple vessel array. For example, a fluidic chip or slide may comprise, e.g., 2 or more multiple vessel arrays, each of which is served by its own filling system.

As used herein a "multiple capillary array" refers to multiple vessel array, wherein the reaction vessels of the array are capillary vessels.

As used herein, the term "sub-volume" as used in reference to a sample or a reaction, refers to a partitioned portion of a sample or vessel. For example, in a multiple vessel array, each of the reaction vessels in the array defines a sub-volume of the total volume in the array. As used in reference to a sample or a reaction, e.g., a nucleic acid detection reaction on a test sample, the term sub-volume refers to a partitioned portion of the reaction, wherein the combined volumes of all the sub-volumes is the total volume of the test reaction on that sample. The total reaction volume is referred to as the "test volume" for that sample. Different sub-volumes of a test volume may be of different volume, or they may be of equal volume.

As used herein, the term "sampling" as used in reference to samples or reactions refers to taking from or partitioning a portion of a sample. For example, sampling a solution containing target nucleic acid molecules may comprise taking or partitioning a liquid portion of the sample, or it may comprise taking or partitioning a portion of the nucleic acid in said sample (e.g., by capturing a sample of the nucleic acid from said solution).

As used herein, the term "sample tray" is used in its broadest sense to refer to any system or substrate wherein a plurality of partitioned reactions may be conducted, including but not limited to microtitre assay plates, microwell slides, fluidic chips, fluidic cartridges and cards, etc. A sample tray is not limited by the nature of the partition, which may comprise closed or opened physical containment (e.g., walls, wells, tubes, etc.) or chemical containment (e.g., in emulsions or suspensions, by use of hydrophobic or hydrophilic zones) or containment by semi-solid containment, e.g., by use of media or components that slows movement, e.g., by restricting diffusion, such as gels or polymers.

As used herein, the term "isolated reaction zone" refers to a portion of a sample tray wherein a reaction is effectively partitioned from other reactions.

As used herein, the term "binding agent," as used in reference to binding molecules, e.g., nucleic acid, encompasses any agent capable of capturing or holding on to a molecule. For example, binding may be by formation of a covalent bond with a molecule, or may be by formation of a non-covalent linkage (e.g., by antibody binding, hybridization, intercalation, binding to a binding partner) or any of the other affinity interactions well known in the art). Binding also encompasses, e.g., capture in a substrate such as a gel matrix, e.g., by diffusion, in which a slow rate of diffusion out of the matrix restricts the bound molecule.

As used herein, the term "variable," as used in reference to binding capacities, binding rates, volumes or sub-volumes, refers to a collection of two or more binding capacities, binding rates, volumes or sub-volumes that differ one from another.

As used herein, the term "serial," as used in reference to binding capacities, binding rates, volumes or sub-volumes refers to variable binding capacities, binding rates, volumes and sub-volumes, wherein, within a collection of three or more binding capacities, binding rates, volumes or sub-volumes, the binding capacities, binding rates, volumes or sub-volumes differ one from another by a multiple of the same factor. For example, a collection of sub-volumes having volumes V, 10V, 100V and 1000V differ by multiples of the factor of 10.

As used herein, the term "binding rate" refers to the rate at which a binding agent will bind a given binding partner, such that the binding agent will bind a particular amount of partner in a particular amount of time, until, e.g., the binding capacity is reached.

As used herein, the term "binding capacity" refers to the total amount of a binding partner that an amount (e.g., a unit or a portion) of binding agent can bind.

As used herein, the term "comparable with," as used in reference to numbers of entities, indicates that the numbers of entities are similar, e.g., that there is less than about 2 orders of magnitude difference between the numbers of each entity. For example, if a number of reaction vessels is comparable to a number of target molecules, then the numbers of reaction vessels and target molecules are within about 2 orders of magnitude of each other.

DETAILED DESCRIPTION OF THE INVENTION

Particular embodiments of the invention are described in the Summary, and in this Detailed Description of the Invention. Although the invention has been described in connection with specific embodiments, it should be understood that the invention as claimed should not be unduly limited to such specific embodiments. For example, the devices and methods of the present invention are described in connection with particular nucleic acid detection methods such as polymerase chain reaction. It should be understood that the present invention is not limited to methods and applications related to the polymerase chain reaction.

For example, in addition to PCR, numerous technologies are known for generating a detectable signal in the presence of a target nucleic acid are known in the art. Some methods comprise amplification using RNA-DNA composite primers (e.g., as disclosed in U.S. Pat. No. 6,251,639, herein incorporated by reference in its entirety). Some methods comprises the use of rolling circle amplification, (e.g., as in U.S. Pat. Nos. 6,210,884, 6,183,960 and 6,235,502, herein incorporated by reference in their entireties), while other methods comprise the creation of DNA product using nucleic acids comprising loop-forming sequences, e.g., as described in U.S. Pat. No. 6,410,278, herein incorporated by reference in its entirety. Other methods that find application with the devices and methods of the present invention include but are not limited to the INVADER assay (Third Wave Technologies, Madison Wis.; see e.g., U.S. Pat. Nos. 5,994,069, and 7,011,944, and de Arruda et al., Expert. Rev. Mol. Diagn. 2(5), 487-496 (2002), all of which are incorporated herein by reference in their entireties)

The present application provides methods and devices for absolute quantification of polymerase chain reaction target nucleic acids. In particular, the methods and devices of the present application provide for splitting a nucleic acid sample to be analyzed into small, isolated volumes, conducting the method of polymerase chain reaction (PCR) on said volumes, detecting PCR amplification products, analyzing said detected PCR amplification products, performing absolute quantification of the PCR target and presenting said quantification results.

Highly accurate, absolute quantification of a PCR target is very important for studies of gene function and pathology in such fields as for example, basic research and biotechnology, and it is mandatory for clinical application of a PCR method. A current approach to absolute PCR quantification is not based on direct measurement of the target copy number, but relies on certain assumptions about efficiency of the reaction at early cycles and on building reliable calibration curves. Methodologically, therefore, real-time PCR analysis is only relatively quantitative.

The method of the present invention provides ultra-sensitive detection and highly accurate absolute quantification of real-time or end point PCR at the single molecule level in nanoliter or sub-nanoliter volumes. One embodiment of the method of the present invention comprises the steps of: 1) serial dilution of a template sample with an unknown original number of template molecules (ONTM) in a PCR reaction mixture, 2) sub-dividing each of said dilutions into a large number of discrete, spatially isolated small sub-volumes, 3) perform PCR amplification in each of said sub-volumes simultaneously such that amplification products generated in each sub-volume are confined in said sub-volumes (FIG. 1), detect the generated amplification products in each discrete, spatially isolated sub-volume, and 4) statistically analyze each of said sub-volumes for: a) the original starting number of template molecules (or concentration) in the PCR mixture and b) the probability of PCR contamination.

It is contemplated that the serial dilution of the template sample ensures that a statistically significant number of the sub-volumes contain single template molecules. As well, sub-division of the template sample into small, isolated sub-volumes further serves to distribute the template sample so that a statistically significant number of said sub-volumes contained single template molecules. It is contemplated that the sub-division of the template sample can be achieved by various methods, including, but not limited to, those methods as described herein. It is contemplated that conducting PCR in said isolated sub-volumes such that the PCR products generated in one sub-volume are confined in that sub-volume enables detection of said single template molecules. It is further contemplated that detection of the PCR products in said isolated sub-volumes is performed either during the PCR cycles (e.g., "real time" detection) or after the PCR amplification is completed (e.g., "end-point" detection). It is additionally contemplated that subsequent statistical analysis of the data generated by detection methods as described herein is targeted to determine the average number of template molecules per one sub-volume $\lambda$ and, based on Poisson statistics, calculate the ONTM and probability of PCR contamination.

The devices for practicing the methods of the present invention are provided to allow for high throughput amplification of multiple target molecules simultaneously. There are several ways to capture data generated in the amplification process whereby detection of template copies can be measured. One such data capture, real-time data capture, occurs throughout the amplification process. The other alternative is to capture data at the end of the amplification, end point data capture.

An example of a device that performs real-time absolute quantitative PCR using the methods of the present invention is depicted in FIG. 6. The template sample is diluted in a PCR mix containing a nucleic acid affinity fluorescent dye (e.g., for example, SYBR® Green) and distributed on a substrate located in proximity, for example, between the aforementioned sub-volume cells. It is contemplated that by performing the aforementioned sample distribution, the average number of target copies per one cell $\lambda$ low, such that there will be many sub-volume cells with negative responses (i.e., no amplification). Once distributed, the substrate undergoes thermal cycling (i.e. polymerase chain reaction). The sub-volumes on the substrate are illuminated by an illumination system (e.g., for example, laser) and emitted fluorescence of the device is projected through an optical system onto a multi-pixel photodetector (e.g., for example, a charge coupled device (CCD), complementary metal oxide semiconductor (CMOS) detector, photomultiplier tube (PMT), or avalanche photodiode (APD) array) and recorded by a computer system. Statistical analysis of sub-volumes that contain "YES" (e.g., amplification products) and "NO" (e.g., no amplification products) events, yields $\lambda$ from which ONTM is calculated. FIG. 2 depicts the two sorts of results, either YES or NO, that are recorded from sub-volumes in a real-time PCR device, depending whether a template molecule was present (YES, FIG. 2A) or not (NO, FIG. 2B).

An example of a device of that serves to perform end point absolute quantitative PCR using the methods of the present invention is similar to the above mentioned device for performing real time PCR. However in end point PCR, illumination of the sub-volumes is only performed after completion of the amplification reaction, and not during the reaction.

For real-time PCR amplification, if it is assumed that the sensitivity of the real time detection system is sufficient for detection of the PCR amplification products obtained from a single copy, then the expected real time PCR curves detected from individual sub-volumes are seen in FIG. 2. It is contemplated that as very low ONTMs per sub-volume ($0.5<\lambda<2$) are used, large variation of the fluorescent signal between individual sub-volumes are realized. Indeed, in most compartments there will not be a target molecule at all, thereby yielding no signal. In other compartments there will be a single copy of the template molecule, in still others there will be two, three, or four copies or more. As the amount of the PCR product is contemplated to be proportional to the original number of copies in the exponential, or semi-log linear, region of PCR curve, the observed PCR curves will fall into several distinct groups, corresponding to different original copy numbers (FIG. 3A). When the separation between the groups is well pronounced, several peaks on a histogram of fluorescence signal F detected in individual sub-volumes (FIG. 3B) are seen. It is equally important that for different $\lambda$ values, there are distinct (characteristic) proportions of sub-volumes with no signal (FIG. 3C).

The distribution function P of highly diluted targets are described by Poisson statistics, such that:

$$P(k) = \frac{\lambda^k}{k!} e^{-\lambda}$$

wherein P(k) is a probability to find a sub-volume containing k copies,
wherein $\lambda$ is an average ONTM per one sub-volume, and
wherein e is the natural log FIG. 3C illustrates the distribution function for $\lambda=1$. Thus, for any given number of detected sub-volumes, by integrating the histogram zones corresponding to different ONTMs per small volume (e.g., 0, 1, 2, 3, 4, etc.), a distribution of the original target molecules in individual sub-volumes is obtained.

Using a log-linear least squares regression, the obtained event frequency can be fit to a Poisson distribution and the mean value for $\lambda$ and test goodness of the fit using $X^2$ can be determined. From $\lambda$, ONTM or initial concentration based on total number of sub-volumes and their total volume is calculated. Comparison of the obtained distribution of the target over sub-volumes with Poisson distribution allows the determination of PCR contamination. It is contemplated that for $\lambda<2$, statistical analysis requires detecting at least 100-200 sub-volumes. For example, if a sub-volume is 10 nl, the total reaction volume necessary for absolute target quantification will be 1-2 μl. Therefore, when $\lambda$ is determined, the original target concentration or ONTM can be easily calculated since the entire reaction volume used for detection or total number of sub-volumes and dilution degree for the native sample are known.

Real-time PCR quantification procedures can be complicated if real time detection data does not yield a histogram with clearly separated maxima. However, it is contemplated that for highly diluted samples, a significant number of sub-volumes will not exhibit any amplification, as no target molecules will be contained therein. In such a scenario, quantification of the target molecules is based on statistical analysis of 'YES'/'NO' results at the end of PCR amplification. For end-point PCR quantification, fluorescence measurement at the end of the PCR cycles indicates either a product of PCR amplification is present in a compartment, meaning this compartment confined one or more target molecules initially ('YES' result), or there is no PCR amplification in a compartment, and thus it did not contain target DNA before PCR ('NO result').

It is contemplated that when a series of N measurements, such that a sample is distributed, or sub-divided, into N sub-volumes, PCR amplification is performed and the presence or absence of amplification product (e.g., via fluorescence measurement) is detected in each sub-volume, the result of each measurement in the series will be 'NO', if there are no PCR products detected in the sub-volume and 'YES', otherwise. Thus, the series can be considered as a sequence of N Bernoulli trials. The result of each series of experiments represents the number of 'empty' sub-volumes k, such that the number of 'NO' results, k, is distributed according to binomial law:

$$P(k) = \binom{N}{k} p^k (1-p)^{N-k},$$

with mean value E(k)=Np, variance var(n)=Np(1−p), and standard deviation $\sigma_n = \sqrt{Np(1-p)}$ where p is the probability of 'NO' result. The estimate for concentration is evaluated as $$\lambda_{EST} = -\log\left(\frac{k}{N}\right).$$

Figure 4:
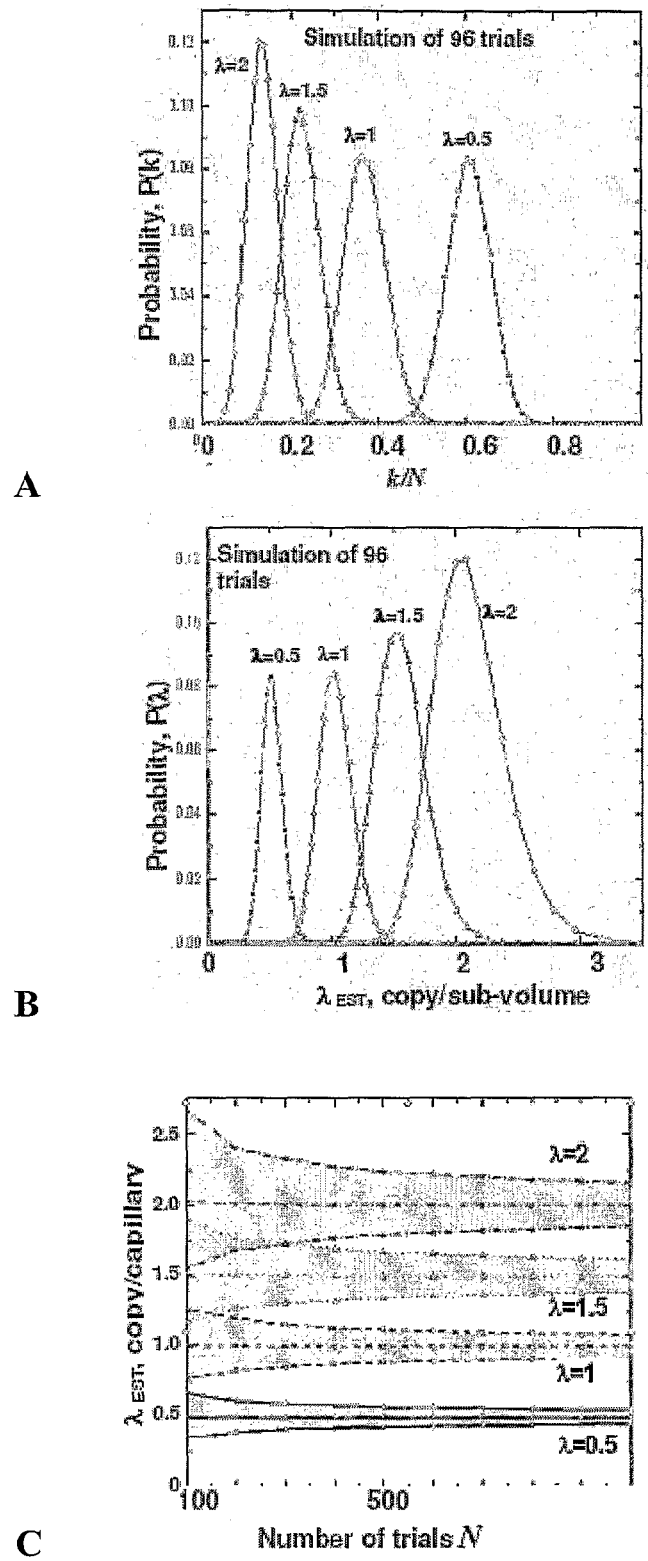
FIGS. 4A, B and C show Monte-Carlo simulations of detecting no target in k of N sub-volumes for mean copy number $\lambda=0.5$, 1, 1.5, and 2. Distribution of 'NO' results, N=96 (A), distribution of estimated $\lambda_{EST}$, N=96 (B), and 95% range depending on number of trials N (C).

A Monte-Carlo simulation of a series of independent experiments, N experiments, in each series are seen in FIG. 4. FIG. 4 demonstrates that even in cases when real-time PCR does not give a clear distinction of signals obtained from each sub-volume during exponential phase of the amplification of single target copies, statistics of 'YES'/'NO' data at the end of PCR allows accurate target quantification for a sufficient number of trials (i.e., sub-volumes) N. For example, FIG. 4C demonstrates that at N=300, 95% confidence intervals are distinct enough to give statistically significant $\lambda$ values, from which ONTM per sample can be easily derived. It is contemplated that for an individual sub-volume of 10 nl where N=1000, total required reaction volume will be only 10 μl, and an entire amplification array (e.g., NMCA, chip) with all 1000 sub-volumes (e.g., in capillaries, chambers, etc.) can be cycled within about 1 hour. The present invention described herein differs from currently available quantification techniques in real-time or end-point PCR instruments, such that in order to apply the same quantification techniques in commercial real-time or end-point PCR instruments, at least 10 ml of a PCR mixture with template would be required and the experiment would take around 10-20 hours.

Calculations to determine the pre-PCR number of target DNA molecules ($M_0$) in a pre-amplification target sample is preformed using the equation:

$$M_0 = N_{sub\text{-}volumes} \times [-\ln(P)]$$

wherein N is the number of sub-volumes, and
wherein P is the percent of sub-volumes that contained to amplification products Standard deviations are further estimated using the equation:

$$\sigma_N = \sqrt{N_{sub\text{-}volumes} P(1-P)}$$

The PCR quantification methods of the present invention collect statistics for single molecule PCR amplification. To obtain accurate statistics, it is contemplated that the method requires at least 100, at least 200, at least 300 hundred DNA molecules amplified in isolated small sub-volumes. Using the methods and devices of the present invention, PCR contamination by contaminant DNA molecules is insignificant if the number of contaminant molecules is smaller than standard deviation $\sigma_N$ of the calculated number of molecules in the sample. Therefore, the present invention differs from current PCR protocols whereby the entire sample is amplified in a single reaction tube, and the contaminants are amplified together with the sample, such that even one contaminant DNA molecule may cause false results because the PCR on that mixture could favor the contaminant, causing the amplified contaminant to mask the presence of the DNA species of interest.

For the present invention, to identify sample contaminants that could impact the outcome of $M_0$, a negative control is assayed along with the unknown template samples, such that all conditions are the same, except the negative control contains no target nucleic acid.

The estimated Poisson parameter $\lambda_{EST}$ is then determined using the following equation:
where:

$$\lambda_{EST} = \ln[P_{CONTROL}(0) / P_{SAMPLE}(0)]$$

Figure 5:
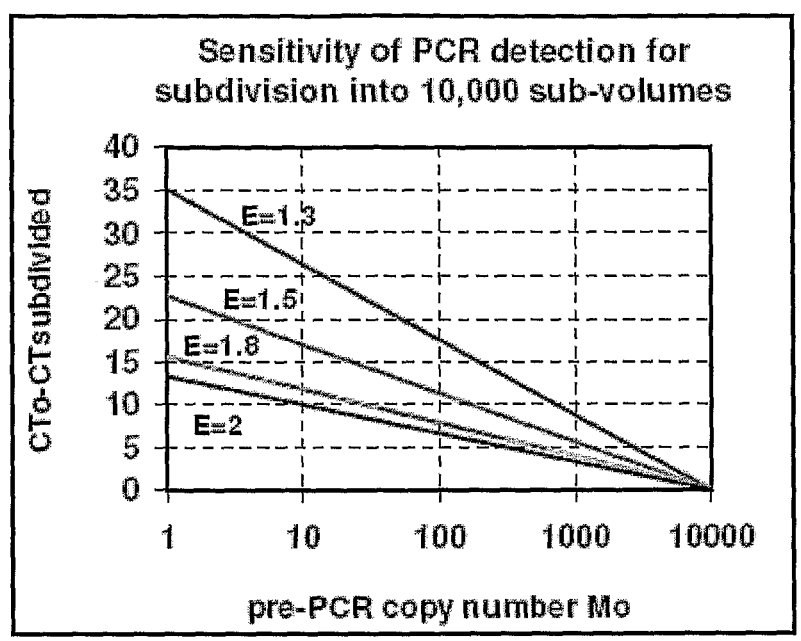
FIG. 5 graph shows the difference between the PCR detection threshold cycle $C_{T0}$ for the original PCR sample and the detection threshold cycle $C_{Tsub\text{-}vol}$ for the sample subdivided into small sub-volumes. Note that when $M_0$ is smaller than the number of sub-volumes, the difference in detection threshold can be very significant. The graph shows that the lower the number of original DNA molecules $M_0$ the greater is the increase in the sensitivity of the PCR detection.

$\lambda_{EST}$ is estimated Poisson parameter $\lambda$ taking into account sample contamination probability
$P_{CONTROL}(0)$ is percent of "0" results in control negative
$P_{SAMPLE}(0)$ is percent of "0" results in tested DNA sample
As used herein, a "0" result is wherein there is no amplicon in a sub-volume. The high level of sensitivity provided by the methods and devices of the present invention for determining the absolute number of pre-PCR target nucleic acid molecules is seen in FIG. 5. In FIG. 5, the calculated difference between the threshold PCR cycle $C_{T0}$ of the original diluted sample and the threshold cycle in sub-volumes $C_{T\ subvol}$ is provided by application of the data to the equation:

$$C_{T0} - C_{Tsubvol} = \frac{\log[V_0 / (V_{subvol} \times M_0)]}{\log(E)}$$

where:
E—PCR efficiency, $C_T$—threshold cycle, V—sample volume $M_0$—pre-PCR number of target copies Therefore, in low volume PCR, amplification products become detectable in earlier cycles and/or at lower reaction efficiencies thereby yielding significantly enhanced sensitivity when utilizing the methods of the present invention.

In one embodiment, the present invention provides for methods and devices performing absolute quantitative end-point PCR (qe-PCR). In some embodiments, a serial dilution of a nucleic acid template, or target, sample which contains a known or unknown original number of target molecules (ONTM) is created in a mixture of PCR reaction components. In some embodiments, the serial dilution is created external to a high-throughput amplification substrate (e.g., slide, gel, tube), whereas in other embodiments the dilutions are created by the partitioning of the sample into sub-volumes, as described herein. In some embodiments, real-time measurements of PCR amplification products (e.g., via fluorescence detection) are taken. In some embodiments, amplification products are measured (e.g., via fluorescence detection) at the end of the PCR cycling. In some embodiments, the amplification of all sub-volumes occurs simultaneously. In some embodiments, the percent of sub-volumes P that yield no amplification products (i.e., 'NO' determination) and the percent of sub-volumes (1−P) that yield amplification products (i.e., 'YES' determination) are determined.

In one embodiment, the present invention provides for a device for performing absolute real-time and end-point PCR. In some embodiments, the device provides for serial dilution of the template sample containing an unknown original number of the template (target) molecules in a PCR mix. In some embodiments, the device provides for a dispenser (e.g., automated dispensing device) for subdividing each serial dilution of the template sample into spatially isolated sub-volumes on a substrate. In some embodiments, the substrate is, for example a micro-well plate, a slide, a chip, or a capillary tube. In some embodiments, the substrate is pre-coated with a matrix (e.g., agarose, MATRIGEL®, collagen) prior to dispensing the samples. In some embodiments, PCR amplification is conducted in said sub-volumes on said substrate, such that the PCR products generated in said sub-volumes are confined to said sub-volumes. In some embodiments, the generated PCR products are detected in each of said sub-volumes after each amplification cycle is completed (e.g., real-time PCR). In some embodiments, the generated PCR products are detected in each of said sub-volumes after completion of the PCR assay (e.g., end point PCR). In some embodiments, the method of detection is fluorescence detection. In some embodiments, the device of the present invention comprises devices that include an excitation light source, a photo receiving system including an optical system for controlling and synchronizing the thermal cycling and the PCR detection processes, processes for transfer, recording and processing of the acquired data.

Method of detecting accumulated PCR product using fluorescence are well known in the art. When the devices provided herein are utilized to conduct nucleic acid amplification reactions, a number of different approaches can be utilized to detect amplified product. Examples of suitable approaches include, for example, the use of intercalating dye, the use of labeled probes in conjunction with 5' nuclease cleavage, and the use of structured probes.

The use of intercalating dyes utilizes fluorogenic compounds that only bind to double stranded DNA. In this type of approach, amplification product (which is generally double stranded) binds dye molecules in solution to form a complex. With the appropriate dyes, it is possible to distinguish between dye molecules remaining free in solution and dye molecules bound to amplification product. For example, certain dyes fluoresce efficiently only when bound to double stranded DNA, such as amplification product. Examples of such dyes include, but are not limited to, SYBR Green and Pico Green (from Molecular Probes, Inc., Eugene, Oreg.), ethidium bromide, propidium iodide, chromomycin, acridine orange, Hoechst 33258, TOTO-1, YOYO-1, and DAPI (4',6-diamidino-2-phenylindole hydrochloride). Additional discussion regarding the use of intercalation dyes is provided, e.g., by Zhu et al., Anal. Chem. 66:1941-1948 (1994), which is incorporated by reference in its entirety.

Fluorogenic nuclease assays are another example of a product quantitation method that can be used successfully with the devices and methods described herein. The basis for this method of monitoring the formation of amplification product is to measure PCR product accumulation using a dual-labeled fluorogenic oligonucleotide probe, an approach frequently referred to in the literature as the "TaqMan" method. The probe used in such assays is typically a short (ca.

20-25 bases) polynucleotide that is labeled with two different fluorescent dyes. The 5' terminus of the probe is typically attached to a reporter dye and the 3' terminus is attached to a quenching moiety, although the dyes can be attached at other locations on the probe as well. The probe is designed to have at least substantial sequence complementarity with the probe-binding site on the target nucleic acid. Upstream and downstream PCR primers that bind to regions that flank the probe binding site are also included in the reaction mixture.

When the fluorogenic probe is intact, energy transfer between the fluorophore and quencher moiety occurs and quenches emission from the fluorophore. During the extension phase of PCR, the probe is cleaved, e.g., by the 5' nuclease activity of a nucleic acid polymerase such as Taq polymerase, or by a separately provided nuclease activity that cleaves bound probe, thereby separating the fluorophore and quencher moieties. This results in an increase of reporter emission intensity that can be measured by an appropriate detector. Additional details regarding fluorogenic methods for detecting PCR products are described, for example, in U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al, Proc. Natl. Acad. Sci. USA 4 88:7276-7280, (1991); and Livak, K. J., et al., PCR Methods and Applications 357-362 (1995), each of which is incorporated by reference in its entirety.

Structured probes (e.g., "molecular beacons") provide another method of detecting accumulated PCR product. With molecular beacons, a change in conformation of the probe as it hybridizes to a complementary region of the amplified product results in the formation of a detectable signal. In addition to the target-specific portion, the probe includes addition sections, generally one section at the 5' end and another section at the 3' end, that are complementary to each other. One end section is typically attached to a reporter dye and the other end section is usually attached to a quencher dye.

In solution, the two end sections can hybridize with each other to form a stem loop structure. In this conformation, the reporter dye and quencher are in sufficiently close proximity that fluorescence from the reporter dye is effectively quenched by the quencher. Hybridized probe, in contrast, results in a linearized conformation in which the extent of quenching is decreased. Thus, by monitoring emission changes for the reporter dye, it is possible to indirectly monitor the formation of amplification product. Probes of this type and methods of their use is described further, for example, by Piatek, A. S., et al., Nat. Biotechnol. 16:359-63 (1998); Tyagi, S, and Kramer, F. R., Nature Biotechnology 14:303-308 (1996); and Tyagi, S. et al., Nat. Biotechnol. 16:49-53 (1998), each of which is incorporated by reference herein in their entirety for all purposes.

It is contemplated that the detection device of the present invention is not limited to fluorescence detection. Indeed, those skilled in the art will understand that other means of detection for monitoring the accumulation of PCR amplifications are equally applicable to the present invention. In some embodiments, a computer and software for statistical analysis capable of performing the calculations as described herein to determine the original number (or concentration) of target molecules initially contained in the template sample further comprise the device of the present invention.

As noted above, methods of quantitating the number of initial target nucleic acid molecules in a sample often comprises performing variable dilutions of the sample, in which an aliquot of the sample is diluted by a factor to make a first diluted sample, the an aliquot of the first diluted sample is then diluted by a factor to make a second diluted sample, and so forth. These are referred to herein as "variable dilutions."

Any desired dilution factor can be used. For example, in some instances, the successive dilutions are performed using dilution factors that vary between the successive dilutions. For example, an initial aliquot may be subject to dilution by a factor of 10 to make a first diluted sample, an aliquot of the first diluted sample may then be diluted by a factor of 5 to make a second diluted sample, an aliquot of which may then be diluted by a factor of 7.5 to make a third diluted sample, and so forth.

In some instances, the same dilution factor is used for each successive dilution. For example, if the factor is 2, the first dilution contains ½ the concentration of analyte as the starting material, the second dilution contains ¼, and so on. Sequential dilutions in which the same dilution factor is used for each dilution are referred to herein as "serial" dilutions. Serial dilutions using factors of 5, 10, or 100 are common in assays of biological molecules.

In any such sequential dilutions, the total dilution factor at any point is the product of the individual dilution factors in each step up to that point.

One source of variation in quantitation of arises from such sequential dilutions. Generally, samples are diluted using a purified diluent, such a saline solution or a buffer. In many instances, samples such as clinical samples comprise a number of components in addition to the nucleic acid in the sample. For example, a sample may contain contaminating (non-target) nucleic acids, proteins, salts, heme, heparin, etc. When such samples are sequentially diluted, the contaminants are also sequentially diluted such that the reaction conditions under which the different dilutions of target nucleic acids are being tested are not truly identical. In addition, introduction of exogenous materials into the samples (e.g., diluents) increases the likelihood of introducing contaminants into the reactions.

One embodiment of the present invention is to provide methods and devices for sampling a test sample without conducting serial dilutions. The invention comprises several different ways of partitioning different volumes of a sample, e.g., serially smaller sub-volumes, so that the benefits of sequential dilution (e.g., finding an amount of a test sample that provides a Poisson parameter $\lambda$ that is in the desired range for a particular method) can be had without the need for actual dilution of the sample.

In one embodiment, the present invention provides for a sample tray, e.g., for performing PCR. In some embodiments, the sample tray is disposable. In some embodiments, the sample tray is divided into many distinct, isolated compartments or zones. In some embodiments, the number of compartments, or wells, in the sample tray is at least 48, at least 96, at least 384. In some embodiments, the wells in the sample tray are coated with a gel substrate such that the volume of the gel substrate is variable from well to well. In some embodiments, the gel substrate volume increases in a manner such that a serial dilution of a nucleic acid sample, when applied, is realized over a series of wells. In some embodiments, the gel substrate is gelatin, agarose, collagen, or Matrigel®. The present invention is not limited to the type of gel substrate used, it is only required that the nucleic acid sample, when applied, is able to diffuse through the gel and that the gel allows for amplification to occur (e.g., does not inhibit the PCR reaction). In some embodiments, the tray is treated with a gel substrate and a nucleic acid sample is applied such that a "dilution" series of the DNA sample is realized, amplification in the tray is allowed to proceed (e.g., by application of the tray to a PCR instrument). In some embodiments, end point PCR product detection is performed (e.g., via fluorescence detection), the data is applied to the Poisson equations as described herein and an absolute quantification and reporting of sample ONTM is performed. In some embodiments, the data acquisition, calculations, quantification and reporting of ONTM results is performed automatically (e.g., on a computer).

In some embodiments, a sample tray is provided that comprises isolated reaction zones that will contain variable quantities of target nucleic acid. In some embodiments, the reaction zones differ in volume, such that, although the absolute concentrations of all components in the reactions in the different zones are identical, the reactions contain different numbers of target molecules. Use of very low volume trays, e.g. fluidic chips, or multiple capillary arrays, means that the variations in the heating dynamics of the different volumes will be negligible, and will have negligible effects on the efficiency, e.g., of PCR.

Similarly, a sample tray can be configured such that the isolated reaction zones comprise a binding agent configured to bind variable amounts of target nucleic acid from a sample. In some embodiments, the binding agents can bind nucleic acid at different, particular rates, such that exposure of the sample tray to a sample for a fixed amount of time permits the isolated reaction zones to bind variable amounts of nucleic acid. In other embodiments, the isolated reaction zones comprise binding agents having different binding capacities, such that exposure of the sample tray to a sample for a period of time to bind available nucleic acids produces isolated reaction zones having variable amounts of bound target nucleic acid. In each of these embodiments, the variability in binding can be by any desired factor, including but not limited to serial factors in which the binding capability of multiple isolated reaction zones each differ by multiples of the same factor.

The following examples are provided in order to demonstrate and further illustrate certain preferred embodiments and aspects of the present invention and are not to be construed as limiting the scope thereof.

EXAMPLES

Example 1

Multi-Capillary Arrays (MCAs) or Chips as PCR Vessels

The detection and absolute quantification of DNA samples will be performed during a real-time PCR amplification of the samples loaded into nano- or picoliter volume capillaries of disposable multi-capillary arrays (FIG. 7), or chips. Capillary electrophoresis will be used in the system that will help to increase the system sensitivity and specificity and to avoid false negative and false positive results.

Figure 7:
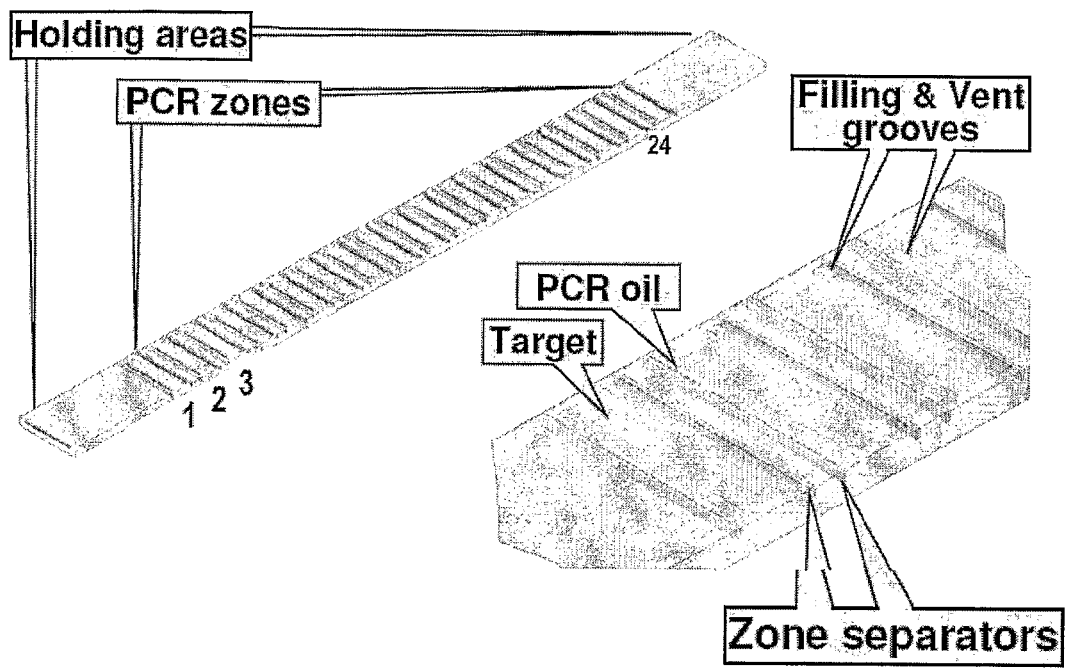
FIG. 7 illustrates one embodiment of the present invention. For example, a monolith multi-capillary array with nanoliter compartments is shown. PCR zones consist of capillary tubes for target samples that are bordered on either side by filling and vent grooves and are separated from adjacent capillary tubes and grooves by zone separators for separation of target samples.

The general view and the enlarged fragment of the MCA are shown in FIG. 7. The array can be divided into many PCR zones. The array in FIG. 7 shows 24 zones (approximately 3 mm long and 10 mm wide), although it is contemplated that MCA may comprise a single zone, or may comprise fewer or more than 24 zones. Each zone is a row of parallel nanoliter to picoliter capillaries, known as a sub-array. By way of example but not by way of limitation, a sub-arrays as described here contains 32 capillaries of 10 nl volume each (100 µm wide, square cross-section, and 1 mm long). More or fewer capillaries may be used a sub-array, depending on the specific configuration of the thermal cycler and/or photo detector. In this embodiment, the capillaries are arrayed in parallel and are bordered by two grooves; a filling groove and a vent groove. The PCR zones are separated by zone separators which block penetration of the DNA samples between individual zones. Similar structures can be organized on glass or silicon chips with scalable microfabrication technology.

A DNA sample to be amplified is loaded the filling grooves of an individual PCR zones. For a serial dilution panel, a DNA sample to be amplified is serially diluted and different dilutions are loaded into different filling grooves of individual PCR zones, one per zone. When the DNA samples are applied to the zone(s) the sample enters (e.g., is taken up by) the capillaries of the sub-arrays due to capillary force. Thus, for example, 32 capillaries of a sub-array are filled with the same DNA sample (total sample volume loaded in one sub-array is approximately 320 nl). Depending on the PCR purpose, one or more zones can be loaded with the same DNA sample. When sample loading is completed, both filling and vent groves may be sealed, e.g., with PCR oil. The loaded MCA is covered with a glass slide and transferred to a PCR device where it undergoes thermal cycling, and either real-time or end point fluorescence is detected for the PCR products generated in all PCR zones.

Example 2

PCR on Matrix Coated Substrates

Figure 8:
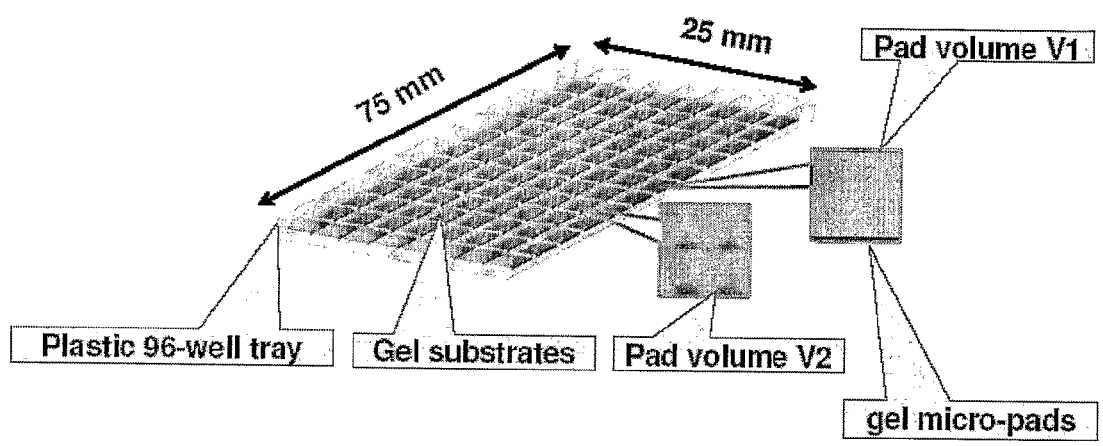
FIG. 8 illustrates one embodiment of the present invention. For example, a disposable sample tray for PCR amplification in polonies is shown. Arrays of gel micro-pads (e.g., gel-substrates) are deposited in the individual compartments of a plastic sample tray. Said arrays may differ both in volumes of individual pads and in composition (porosity) of gels of which the pads are formed. DNA samples are loaded in the compartments of the tray, the tray is covered by a lid, and thermal cycling using an end-point cycler is performed. The sample tray is made of scannable optically transparent plastic such that scanning can be performed from above or below with a laser beam or LED arrays.

PCR can be performed in a disposable sample tray with arrays of gel micro-pads as depicted in FIG. 8. For example, serial dilutions of DNA samples in a PCR mix are made, aliquoted to a multi-well plate and covered with mineral oil in order to avoid the sample evaporation. The samples are then loaded from the plate into individual cells of the disposable sample tray with the gel pad arrays. The DNA samples are allowed to infuse into the gel pads. For example, the samples are allowed in infuse into the gel pads at 60° C. for 5-30 minutes. After infusion of the sample DNA into the gel pad, the pad is washed to remove any remaining sample. Mineral oil or another sealing compound is applied to the top of the gel pad to seal the PCR template and generated PCR products in the gel pad (Tillib et al., 2001, Anal. Biochem. 292:155). If a polymer is used to seal the gel pad, the polymer may be allowed to solidify before proceeding with PCR. PCR is carried out to an end point read. PCR generated products are detected in the gel pads, and P percent is determined and ONTM calculated for each individual gel pad array.

PCR amplification can also occur on glass or plastic substrates with deposited non-denaturing gel/matrix as depicted in FIG. 9. The present invention takes advantage of the idea that the progeny of a single template molecule (called a 'polony') occupies the smallest possible volume due to poor diffusion of DNA molecules through the gel/matrix. As a result, the polony's spot has very a high concentration of PCR generated products (Mitra and Church, 1999, Nucl. Acids Res. 27:e34).

Example 3

PCR in Water/Oil Emulsions

Serial dilutions of a DNA sample in PCR mix are prepared and placed into a vial and covered with oil. Emulsification of the PCR mix and oil is preformed such that an emulsion is created and the bubbles are capable of withstanding PCR thermal cycling. The emulsified samples are loaded into a capillary tube and end point PCR is carried out in the tube.

PCR generated products are detected in the bubbles, P percent of bubbles with no PCR amplification products associated with them is determined and ONTM is calculated as described herein.

Example 4

PCR on Beads in Water/Oil Emulsions

Serial dilutions of a DNA sample in PCR mix are prepared, placed into a vial and covered with oil. Beads are added to the dilutions and the DNA is allowed to attach to the beads. Emulsification is carried out in that the beads are surrounded by water, and the water surrounded by oil so that an emulsion is created and the bubbles are capable of withstanding PCR thermal cycling. The emulsified samples are loaded into a capillary tube, and end point PCR is performed. The PCR generated products are detected in the water bubbles, P percent of beads with no amplification products associated with them is determined and ONTM is calculated.

Example 5

PCR on Liquid Polymer Beads

Figure 10:
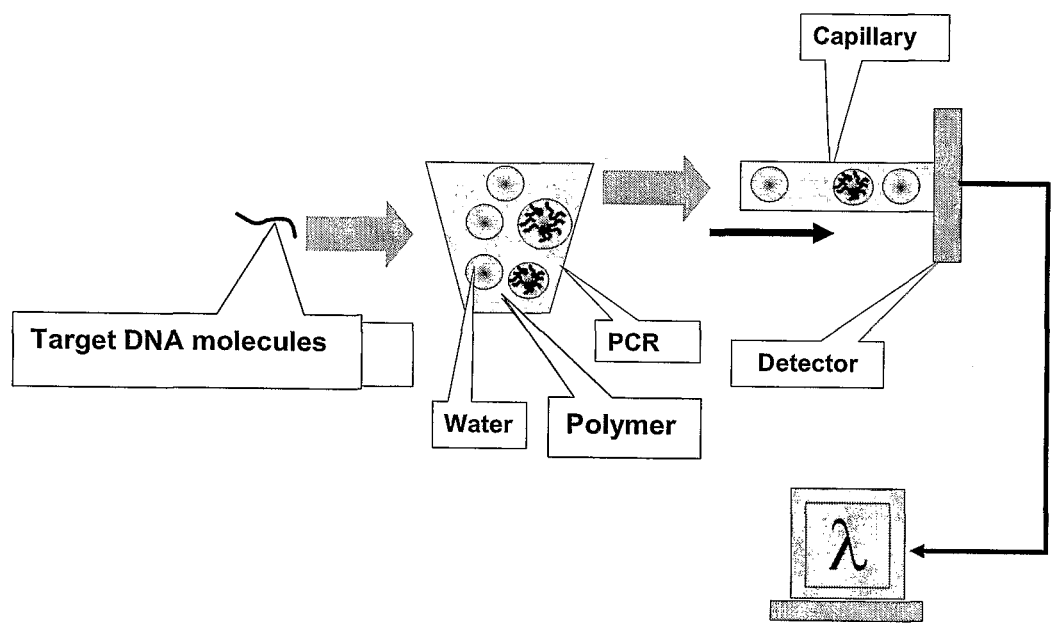
FIG. 10 diagrams steps for PCR on beads immersed in a liquid polymer. Beads with attached DNA are put into a vial with PCR mix diluted in liquid polymer having a certain DNA diffusion coefficient. Conditions are selected to assure that concentration of beads is such that the average distance between beads significantly exceeds the possible diffusion distance of amplified DNA segments in the PCR mix diluted in liquid polymer. After PCR is completed, the beads with DNA samples from the vial are loaded into a capillary and PCR product is detected. Determined percent P of beads that yielded no PCR amplification allows calculation of pre-PCR number of DNA molecules $M_0$ using statistical analysis.

In a vial (see, e.g., FIG. 10), a PCR mix is prepared which includes a liquid polymer with a known DNA diffusion coefficient. The target DNA is attached to beads, and the DNA beads are added to the PCR mix with liquid polymer. The concentration of beads should be such that the average distance between beads significantly exceeds the diffusion length of target DNA fragments in said PCR mix diluted in liquid polymer. Aliquots of the samples are loaded into a capillary tube and end point PCR is performed. PCR products generated are detected and P percent of beads which yielded no PCR amplification products is determined and ONTM calculated.

Example 6 qPCR and Reduction of Manual Serial Dilutions

On the same tray, gel substrates in different cells of the sample tray (FIG. 8) can differ in thickness, geometry (e.g., solid substrates or arrays of gel micro-pads), and/or composition (e.g., gels can differ in content of polymer, cross-linker, etc.). Specific configuration of the gel substrates and specific sets of gel substrates on the sample tray provides different ways for performing PCR quantification.

For example, arrays of gel micro-pads that differ in pad volume (FIG. 8) can be used to avoid manual serial dilution of a DNA sample. Indeed, an original DNA concentration per one pad in pads of volume V1 will differ from the original DNA concentration per one pad in pads of volume V2 by the factor V1/V2. Effectively, this is the same as placing different dilutions of DNA sample in arrays with identical pad volume V. As well, using solid gel substrates that differ in gel composition (e.g., for example, different content of polymer and cross-linker) is equally amenable. The infusion of DNA samples into gel proceeds at different speed depending on the gel concentration, and by using an appropriate calibration the same density of polonies for different DNA content can be obtained thereby avoiding the necessity of preparing and distributing serial dilutions.

Example 7

Design, Fabrication and Use of Multi-Capillary Arrays

Figure 11:
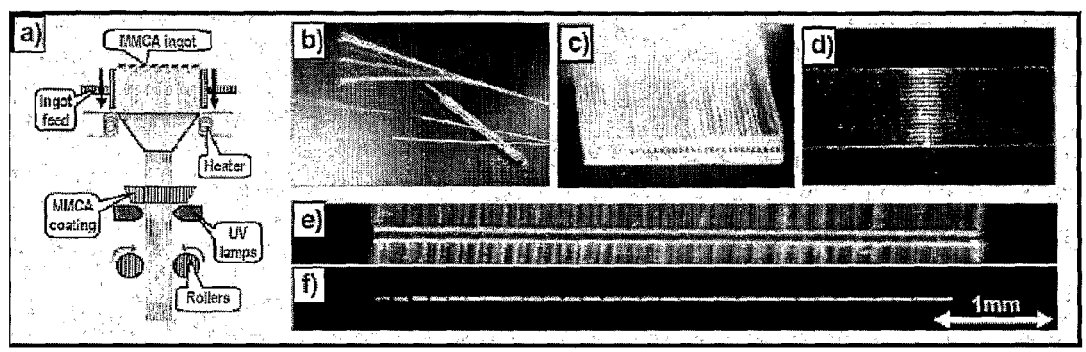
FIG. 11 demonstrates an embodiment of the present invention. For example, manufacture and characteristics of monolith multi-capillary arrays is illustrated; a) shows a general flow scheme of how a multiple micro-capillary array (MMCA) substrate is created, b) shows the general view of the capillary tubes, (c) shows the capillary tube array in cross section; d) and f) shows top view fluorescence of 16- and 32-capillary arrays; and (e) shows a 32-capillary array with opened filling V-groove.

A process that produces monolith capillary arrays with or without split ends is illustrated in FIG. 11. For example, a set of glass ferrules, their number equal to the desired number of capillaries required, is utilized to create the multi-capillary array. The size of the ferrules and the thickness of their walls is chosen depending on the desired inner size of the capillaries and the spacing between them. The ferrules are pressed together into a planar array and are drawn at an elevated temperature. Due to adhesion, the resulting array has a truly monolithic structure. The production process allows formation of extremely regular arrays of square or rectangular capillaries with an ideal translational symmetry. Being monolithic, the array acts as a low loss medium for the propagation of light. Its optical properties ensure a uniform illumination of all capillaries, thereby facilitating focusing a laser beam on the center of the capillary. Significant advantages of the multi capillary arrays include low cost of manufacture and the absence of any specially adjusted parts in the detection zone.

Thirty-two capillary arrays are fabricated with 100, 150 and 200 μm square capillary cross section, 300 μm array pitch, 0.5-1 mm thickness, 10 mm width and 90 mm length. Using laser engraving instrumentation, sub-arrays can be formed of nano-volume capillaries by making V-grooves across the top surface of the MCA for loading of nucleic acid samples into nano-volume wells and for venting air (see FIG. 7). The size of the V-grooves can be chosen to accommodate nucleic acid samples volumes that allow for filling of the 32 capillaries. For example, for a 100 μm cross-section and a 10 nl capillary volume, the V-grooves will be 500 μm wide, 200 μm deep and separated by 1.2 mm. In order to create the multiple PCR zones (FIG. 7), separation zones can be formed across the MCA. These zones will define size/volume of the sub-arrays and sub-volumes, respectively. For example, the zones can be formed either by melting glass with a laser across the arrays thereby creating focal plugs inside the capillaries, or by laser engraving grooves across the array and filling the grooves with UV curable optical glue. Both laser engraving and filling separators with UV curable glue can be performed automatically. The automatic procedures utilized yield a low cost, disposable device of the present invention.

Example 8

An Application for Calculating Results

The reported results from Mitra and Church, 1999, Nucl. Acids Res. 27:e34 were applied to the Poisson equations of the present invention to demonstrate the increased accuracy for determining ONTM using the methods of the present invention for processing experimental results. Images of gel slides with polonies (FIG. 9) were used. The slide surface was divided into cells of the size of polonies (approximately 300 mkm) and the fraction of empty cells was found in order to determine $\lambda_{EST}$. The calculated number of polonies grown on gel slides were determined by using the methods of the present invention and the numbers were compared with the number of polonies as manually counted by Mitra and Church (see graph, FIG. 9). The calculated polony number was more accurate that just counting colonies, and as the concentration of template DNA increased (e.g., increase in ONTM), the discrepancy between counted colonies and the calculated colonies increased.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of determining the number of target nucleic acid molecules in a sample, comprising:
    a) providing a sample containing a plurality of target nucleic acid molecules, the total number of target nucleic acid molecules being unknown;
    b) diluting said sample to create a plurality of diluted samples;
    c) applying said diluted samples to a multiple vessel array comprising a plurality of reaction vessels, wherein each of said reaction vessels receives an essentially equal sub-volume of one of said diluted samples, wherein the combined volumes of said sub-volumes defines a tested volume, and wherein, as the result of said diluting, the number of said plurality of reaction vessels exceeds the number of target nucleic acid molecules in said tested volume;
    d) treating said multiple vessel array with polymerase chain reaction (PCR) amplification reagents and conditions to produce a detectable signal in the presence of said target nucleic acid;
    e) determining how many of said reaction vessels contain reactions that produce and do not produce said detectable signal; and
    f) determining the number of target nucleic acid molecules in said sample of step a) using the equation:

$$M_0 = N_{sub\text{-}volumes} \times [-\ln(P)]$$

wherein $M_0$ is the number of target molecules in said tested volume,
    wherein N is the number of sub-volumes, and
    wherein P is the percent of sub-volumes lacking said detectable signal.

2. The method of claim 1, wherein said multiple vessel array is a multiple capillary array, and wherein said reaction vessels are capillary reaction vessels.

3. The method of claim 1, wherein said diluting comprises serial diluting.

4. The method of claim 3, wherein at least 200 sub-volumes are made in step c).

5. The method of claim 3, wherein sub-volumes in said multiple vessel array comprise between 1 and 10 nanoliters.

6. The method of claim 5, wherein said reagents are dried prior to exposure to said sample.

7. The method of claim 1, wherein said determining is conducted after the completion of a plurality of cycles of said polymerase chain reaction.

8. The method of claim 1 or claim 2, wherein said detectable signal comprises fluorescence.

9. The method of claim 1, wherein said reagents comprise an oligonucleotide probe comprising a fluorescent moiety.

10. The method of claim 9, wherein said oligonucleotide probe further comprises a quencher moiety.

11. The method of claim 1 or claim 2, wherein said reagents comprise a nucleic acid intercalating dye.

12. The method of claim 1 or 2, wherein a standard deviation in the number of target molecules in a sample is calculated using the equation:

$$\sigma_N = \sqrt{N_{sub\text{-}volumes} P(1-P)}$$

wherein $\sigma_N$ is the standard deviation.

13. The method of claim 1 or 2, wherein said sample is a test sample, further comprising providing a negative control sample lacking said target nucleic acid, wherein said negative control sample is treated identically to said test sample, wherein the Poisson parameter for said test sample is estimated using the equation:

$$\lambda_{EST} = \ln[P_{CONTROL}(0) / P_{SAMPLE}(0)]$$

wherein:
    $\lambda_{EST}$ is the estimated Poisson parameter for said test sample;
    $P_{CONTROL}(0)$ is the percent of reaction vessels lacking signal in the control negative assay; and
    $P_{SAMPLE}(0)$ is the percent of reaction vessels lacking signal in said test DNA sample.

14. The method of claim 2, further comprising communicating the determined number of capillary reaction vessels containing reactions producing said detectable signal to a computer, wherein a calculation is performed by said computer.

* * * * *